US005766920A

United States Patent [19]
Babbitt et al.

[11] Patent Number: 5,766,920
[45] Date of Patent: Jun. 16, 1998

[54] EX VIVO ACTIVATION OF IMMUNE CELLS

[75] Inventors: Bruce P. Babbitt, Easton; Zhengyi J. Zhang, Needham, both of Mass.

[73] Assignee: Cellcor, Inc., Newton, Mass.

[21] Appl. No.: 370,287

[22] Filed: Jan. 6, 1995

Related U.S. Application Data

[63] Continuation-in-part of Ser. No. 214,400, Mar. 16, 1994, Pat. No. 5,569,585, which is a continuation-in-part of Ser. No. 30,607, Mar. 12, 1993, abandoned, which is a continuation-in-part of Ser. No. 963,486, Oct. 21, 1992, abandoned, said Ser. No. 370,287, is a continuation-in-part of Ser. No. 188,262, Jan. 27, 1994, which is a continuation-in-part of Ser. No. 936,730, Aug. 31, 1992, abandoned, which is a continuation of Ser. No. 518,322, May 7, 1990, abandoned, which is a continuation of Ser. No. 68,413, Jul. 1, 1987, abandoned, which is a continuation-in-part of Ser. No. 696,546, Jan. 30, 1985, Pat. No. 4,716,111, which is a continuation of Ser. No. 407,236, Aug. 11, 1982, abandoned, said Ser. No. 370,287, is a continuation-in-part of Ser. No. 300,982, Sep. 6, 1994, abandoned, which is a continuation of Ser. No. 975,682, Nov. 13, 1992, abandoned, which is a division of Ser. No. 747,484, Aug. 19, 1991, Pat. No. 5,192,537, which is a continuation of Ser. No. 681,668, Apr. 8, 1991, abandoned, which is a continuation of Ser. No. 405,044, Sep. 11, 1989, abandoned, which is a continuation of Ser. No. 903,489, Sep. 4, 1986, abandoned, which is a continuation-in-part of Ser. No. 595,081, Mar. 30, 1984, abandoned.

[51] Int. Cl.$^6$ .................... C12N 5/00; C12N 5/08
[52] U.S. Cl. .................... 435/240.1; 435/240.2; 435/240.21; 935/108
[58] Field of Search .................... 435/240.1, 240.21, 435/240.2; 935/108

[56] References Cited

U.S. PATENT DOCUMENTS

| | | | |
|---|---|---|---|
| 4,172,124 | 10/1979 | Koprowski et al. | 424/85 |
| 4,211,766 | 7/1980 | Bjorklund | 424/88 |
| 4,361,550 | 11/1982 | Kung et al. | 424/85 |
| 4,404,280 | 9/1983 | Gillis | 435/68 |
| 4,444,887 | 4/1984 | Hoffmann | 435/240 |
| 4,451,570 | 5/1984 | Royston et al. | 435/240 |
| 4,474,876 | 10/1984 | Osband et al. | 435/4 |
| 4,690,915 | 9/1987 | Rosenberg | 514/2 |
| 4,704,273 | 11/1987 | McMichael | 424/85 |
| 4,710,380 | 12/1987 | Gottlieb | 424/101 |
| 4,716,111 | 12/1987 | Osband et al. | 435/68 |
| 4,778,750 | 10/1988 | Gottlieb | 435/5 |
| 4,849,329 | 7/1989 | Leung et al. | 435/2 |
| 4,876,193 | 10/1989 | Gottlieb | 435/29 |
| 5,026,365 | 6/1991 | Rossini et al. | 604/891 |
| 5,192,537 | 3/1993 | Osband | 424/85 |
| 5,316,763 | 5/1994 | Ochoa et al. | |

FOREIGN PATENT DOCUMENTS

| | | |
|---|---|---|
| WO 87/05400 | 9/1987 | WIPO. |
| WO 88/02774 | 4/1988 | WIPO. |

OTHER PUBLICATIONS

Abb, J., et al., "Lymphocyte Activation by the Tumor–Promoting Agent 12–O–Tetradecanoylphorbol–13–Acetate (TPA)", *J. Immunology*, 122:1639–1642.

McCrady, C., et al., "Alteration of Human Lymphokine–activated Killer Cell Activity by Manipulation of Protein Kinase C and Cytosolic $Ca^{2+1}$", 1988, *Cancer Research*, 48:635–640.

Chatenoud, L., et al., "Restriction of the Human in Vivo Immune Response Against the Mouse Monoclonal Antibody $OKT3^1$", 1986, *J. Immunology*, 137:830–38.

Kradin, R., et al. "Tumour–Infiltrating Lymphocytes and Interleukin–2 in Treatment of Advanced Cancer", 1989, *The Lancet*, I:577–80.

Margolin, K., et al., "Interleukin–2 and Lymphokine–Activated Killer Cell Therapy of Solid Tumors: Analysis of Toxicity and Management Guidelines", 1989, *J. Clin. Oncology*, 7:486–98.

Rosenberg, S., et al., "A New Approach to the Adoptive Immunotherapy of Cancer with Tumor–Infiltrating Lymphocytes", 1986, *Science*, 233:1318–1321.

Rosenberg, S., et al., "Observations on the Systemic Administration of Autologous Lymphokine–Activated Killer Cells and Recombinant Interleukin–2 to Patients with Metastatic Cancer", 1985, *N.E. J. Medicine*, 313:1485–92.

Rosenberg, S., "Adoptive Immunotherapy of Cancer Using Lymphokine Activated Killer Cells and Recombinant Interleukin–2", *Important Advances in Oncology*; DeVita et al., (eds.); J.B. Lippincott Company, Philadelphia, 1986, Ch. 4, pp. 55–91.

Schoof, D., et al., "Adoptive Immunotherapy of Human Cancer Using Low–Dose Recombinant Interleukin 2 and Lymphokine–activated Killer Cells", 1988, *Cancer Res.*, 48:5007–10.

Seder, R., et al., "Acquisition of Lymphockine–Producing Phenotype by $CD4^+$ T Cells", 1994, *Annual Rev. of Immunology*, 12:635–73.

Siegel, J., et al., "Interleukin–2 Toxicity", 1991, *J. Clin. Oncology*, 9:694–704.

Spiess, P., et al., "In Vivo Antitumor of Tumor–Infiltrating Lymphocytes Expanded in Recombinant Interleukin–2", 1987, *J. Nat'l Cancer Institute*, 79:1067–75.

Vigeral, P., et al., "Prophylactic Use of OKT3 Monoclonal Antibody in Cadaver Kidney Recipients", 1986, *Transplantation*, 41:730–33.

West, W., et al., "Constant–Infusion Recombinant Interleukin–2 in Adoptive Immunotherapy of Advanced Cancer", 1987, *N.E. J. Medicine*, 316:898–905.

Abb et al., "Lymphocyte Activation by the Tumor–Promoting Agent 12–0–Tetradecanoylphorbol–13–Acetate (TPA)", J. of Immunology 122:1639–1642, 1979.

(List continued on next page.)

*Primary Examiner*—Frank C. Eisenschenk
*Attorney, Agent, or Firm*—Fish & Richardson P.C.

[57] ABSTRACT

Disclosed is a process of activating patient-derived mononuclear cells by exposing the cells in vitro to substances wo generate immunoreactive cells. The ex vivo activated cells are then reinfused into the patient to enhance the immune system to treat various forms of cancer, infectious diseases, autoimmune diseases or immune deficiency diseases.

17 Claims, 6 Drawing Sheets

OTHER PUBLICATIONS

Abulafia et al., "In Vitro Production of T Cells Immunoreactive Against Prostate Specific Antigen:A Novel Approach for an Antigen-Specific Adoptive . . . ", Am. Soc. for Biochemistry & Molecular Biology 1896, 1990.

Aliski et al., "The Regulation of Living Cell Therapies (Biocare)", Regulatory Affairs 3:639–650, 1991.

Carpinito et al., "Successful Adoptive Immunotherapy of Cancer Using In Vitro Immunized Autologous Lymphocytes and Cimetidine", Am. College of Surgeons 1986 Surgical Forum 27:418–421, 1986.

Cavagnaro et al., "Successful In Vitro Primary Immunization of Human Peripheral Blood Mononuclear Cells and its Role in the Development of Human-Derived Monoclonal Antibodies", Biotechniques 1:30–36, 1983.

Celis et al., "Peptide-Induced Proliferation and Lymphokine Production in Human T Cells in the Absence of Antigen-Presenting Cells:Role of T-Cell Activation State and . . . ", Human Immunology 34:173–180, 1992.

Darrow et al., "Modulation of In Vitro Autologous Melanoma-Specific Cytotoxic T-Cell Responses by Phorbol Dibutyrate and Ionomycin", Cellular Immunology 125:508–517, 1990.

Delfraissy et al., "Primary in Vitro Antibody Response from Human Peripheral Bloody Lymphocytes", J. of Immunology 118:630–635, 1977.

du Moulin et al., "Quality Assurance and Quality Control (QA/QC) in Biocare, Autolymphocyte Therapy as a Model", Clinical Immunology Society, 1989.

du Moulin et al., "Implementation of an Effective Program for Quality Assurance and Quality Control in Living Cell Therapy:A 2-Year Experience with . . . ", Transplantation Proceedings 24:2802–2808, 1992.

du Moulin et al., "Use of Limulus Amebocyte Lysate (LAL) Assay in Living Cell Therapies", Biopharm, 1992.

du Moulin et al., "Quality Assurance/Quality Control Compliance Program:A Cellular Therapy Developer's Perspective", Regulatory Affairs 5:461–472, 1993.

Fauci et al., "Activation of Human B Lymphocytes. I. Direct Plaque-Forming Cell Assay for the Measurement of Polyclonal Activation and Antigenic Stimulation of . . . ", J. of Experimental Medicine 144:674–684, 1976.

Feinfeld et al., "Interstitial Nephritis in a Patient Receiving Adoptive Immunotherapy with Recombinant Interleukin-2 and Lymphokine-Activated Killer Cells", Am. J. Nephrol 11:489–492, 1991.

Frenster et al., "In-Vitro Activation and Reinfusion of Autologous Human Lymphocytes", The Lancet 979–980, 1968.

Geha et al., "Interaction of Human Thymus-Derived And Non-Thymus-Derived Lymphocytes in Vitro", J. of Experimental Medicine 138:1230–1247, 1973.

Gifford et al., "Cimetidine-Induced Augmentation of Human Lymphocyte Blastogenesis by Mitogen, Bacterial Antigen and Alloantigen", Biological Abstracts 70:4655, 1980.

Graham et al., "The Use of Ex Vivo-Activated Memory T Cells (Autolymphocyte Therapy) in the Treatment of Metastatic Renal Cell Carcinoma:Final Results From a Randomized, . . . ", Seminars in Urology 11:27–34, 1993.

Hirai et al., "Temperature Influences on Different Human Alpha Interferon Activities", J. of Interferon Research 4:507–516, 1984.

Hoffman, "Antigen-Specific Induction and Regulation of Antibody Synthesis in Cultures of Human Peripheral Blood Mononuclear Cells", Proc. Natl. Acad. Sci. USA 77:1139–1143, 1980.

Kanazawa et al., "Serum from Patients with Autoimmune Diseases Induces in Vitro Production of Disease-Associated Antibodies by Peripheral Blood . . . ", J. of Clinical Endocrinology and Metabolism 63:683–688, 1986.

Kessler et al., "Regulation of Somatic-Cell Therapy and Gene Therapy by the Food and Drug Administration", The New England J. of Medicine 329:1169–1173, 1993.

Krane et al., "Treatment of Metastatic Renal Cell Carcinoma with Autolymphocyte Therapy, Low Toxicity Outpatient Approach to Adoptive Immunotherapy Without Use . . . ", Urology 35:417–422, 1990.

Lavin et al., "Autolymphocyte Therapy for Metastatic Renal Cell Carcinoma:Initial Clinical Results From 335 Patients Treated in a Multisite Clinical Practice", Transplantation Proceedings 24:3059–3064, 1992.

Lotze et al., "Lysis of Fresh and Cultured Autologous Tumor by Human Lymphocytes Cultured in T-Cell Growth Fact", Cancer Research 41:4420–4425, 1981.

Lotze et al., "In Vitro Growth of Cytotoxic Human Lymphocytes. II. Use of T Cell Growth Factor (TCGF) to Clone Human T Cells", The J. of Immunology 124:2972–2978, 1980.

Lotze et al., "The In Vitro Distribution of Autologous Human and Murine Lymphoid Cells Grown in T Cell Growth Factor (TCGF):Implications for the Adoptive . . . ", The J. of Immunology 125:1487–1493, 1980.

Mazumder et al., "Lysis of Fresh Human Solid Tumors by Autologous Lymphocytes Activated In Vitro with Lectins", Cancer Res. 42:913–918, 1982.

McCrady et al., "Alteration of Human Lymphokine-Activated Killer Cell Activity by Manipulation of Protein Kinase C and Cytosolic Ca", Cancer Research 48:635–640, 1988.

Nanda et al., "Characteristics of Histamine Receptors Present on Suppressor T Cells in Healthy Individuals", Int J Immuno=Pharmacol 7:587–596, 1985.

Oppenheim et al., "Interleukins & Interferons", Lange Medical Publications 86–90, 1989.

Osband et al., "Successful Tumor Immunotherapy with Cimetidine in Mice", The Lancet 636–638, 1981.

Osband et al., "Effective Treatment of Metastatic Cancer With In Vitro Immunized Autologous Lymphocytes and Cimetidine", Clinical Research 33:457A, 1985.

Osband et al., "Successful Immunization by Infusion of In Vitro Primary Immunized Autologous Lymphocytes", The American Society of Hematology, 1985.

Osband et al., "Autolymphocyte Therapy", Medical Hypotheses 26:259–262, 1988.

Osband et al., Successful Adoptive Immunotherapy of Metastatic Renal Cell Carcinoma With In Vitro Immunized Autologous Lymphocytes and Cimetidine, World J. Urol 4:217–221, 1986.

Osband et al., "Improved Adoptive Cell Immunotherapy by Pre-Infusion Depletion of Suppressor Cells and In Vivo Suppressor Cell Blockade", ASCO, 1986.

Osband et al., "Biocare:Exploiting Biotech's Potential in Special Therapies", The Medical Business Journal 4, 1988.

Osband et al., "Autolymphocyte Therapy:Previous Experience and Future Prospects", Pathol Immunopathol Res 7:483–493, 1988.

Osband et al., "In Vitro Generation of Suppressor Cells, in Both Human and Murine Models, That Block the Proliferative and Cytotoxic Response to Alloantigen:A New Approach . . . ", Clincal Research 37:417a, 1989.

Osband et al., "The Last Word/Biocare:Public Policy Issues for an Emerging Industry", Bio/Technology 8:880, 1990.

Osband et al., "Biocare:Biotechnology in the Clinical Practice of Medicine", Clinical Research 38:5–9, 1990.

Osband et al., "Effect of Autolymphocyte Therapy on Survival and Quality of Life in Patients with Metastatic Renal–Cell Carcinoma", The Lancet 335:994–998, 1990.

Osband et al., "Problems in the Investigational Study and Clinical Use of Cancer Immunotherapy", Immunology Today 11:193–195, 1990.

Osband et al., "Autolymphocyte Therapy:Demonstration of Antigen–Specific Adoptive Immunotherapy", Pediatric Research 25:155A, 1989.

Palacios et al., "Cimetidine Abrogates Suppressor T Cell Function In Vitro", Immunol. Lett. 3:33–37, 1981.

Riddell et al., "Restoration of Viral Immunity in Immunodeficient Humans by the Adoptive Transfer of T Cell Clones", Science 257:238–241, 1992.

Rosenberg et al., "In Vitro Growth of Murine T Cells, II. Growth of In Vitro Sensitized Cells Cytotoxic for Alloantigens", The Journal of Immunology 121:1951–1955, 1978.

Rosenberg et al., "In Vitro Growth of Murine T Cells, IV. Use of T–Cell Growth Factor to Clone Lymphoid Cells", Cellular Immunology 54:293–306, 1980.

Rosenberg, "Adoptive Immunotherapy of Cancer:Accomplishments and Prospects", Cancer Treatment Reports 68:233–255, 1984.

Rosenberg et al., "A New Approach to the Adoptive Immunotherapy of Cancer with Tumor–Infiltrating Lymphocytes", Science 233, 1986.

Rosenberg et al., "A Progress on the Treatment of 157 Patients with Advanced Cancer Using Lymphokine–Activated Killer Cells and Interleukin–2 or . . . ", The New England Journal of Medicine, 316:898–897, 1987.

Rosenberg et al., "Use of Tumor–Infiltrating Lymphocytes and Interleukin–2 in the Immunotherapy of Patients with Metastatic Melanoma", The New England Journal of Medicine, 319:1676–1680, 1988.

Ross et al., "Autolymphocyte Therapy of Metastatic Renal Cell Carcinoma Results in Significant Survival Prolongation with Good Quality of Life:Results . . . ", Am. Soc. for Biochemistry & Molec. Biology, 1487, 1990.

Ross et al., "Autolymphocyte Therapy:An Outpatient, Low-–Toxicity Approach to Adoptive Immunotherapy", Springer–Verlag Berlin Heidelberg, 186–191, 1989.

Ross et al., "Adoptive Immunotherapy of Hormone–Refractory, Stage D2 Prostate Cancer Using Ex Vivo Activated Autologous T Cells (Autolymphocyte Therapy):Results from . . . ", Biotechnology Therapeutics 4:197–211, 1993.

Strausser et al., "In Vitro Growth of Cytotoxic Human Lymphocytes, I. Growth of Cells Sensitized In Vitro to Alloantigens", The Journal of Immunology 121:1491–1495, 1978.

Strausser et al., "Lysis of Human Solid Tumors by Autologuos Cells Sensitized In Vitro Alloantigens", Journal of Immunology 266–271, 1981.

Suciu–Foca et al., "Impaired Responsiveness of Lymphocytes and Serum–Inhibitory Factors in Patients with Cancer", Cancer Res. 33:2373–7, 1972.

Zhang et al., "Synergistic Effects of Autologous Cytokines and OKT3 in the Activation of Human T Cells Used for Adoptive Immunotherapy", J. Immunology 150:218a, 1993.

Osband et al., The Lancet, 335:994–998 (1990).

Feinfeld et al., "Intersitial nephritis in a patient receiving adoptive immunotherapy with recombinant interleukin–2 and lymphokine–activated killer cells," Am. J. Nephrology, 11:489–492.

Rosenberg and Lotze, "Cancer immunotherapy using interleukin–2 and interleukin–2 activated lymphocytes," Annual Review of Immunology, 4:681–709 (1986).

Rosenberg et al., "A new approach to the adoptive immunotherapy of cancer with tumor–infiltrating lymphocytes," Science, 233:1318–1321 (1986).

Darrow et al., "Modulation of In Vitro Autologous Melanoma–Specific Cytotoxic T–Cell Responses by Phorbol Dibutyrate and Ionomycin," Cellular Immunology 125:508–517 (1990).

R. Champlin and R.P. Gale, Bone Marrow Transplantation: Its Biology and Role as Treatment for Acute and Chronic Leukemias; in Normal and Neoplastic Blood Cells: From Genes to Therapy, C. Peschle, Editor, Annals of the New York Academy of Sciences, vol. 511, pp. 447–458 (1987).

Spiegel, R.J., "The alpha interferons: Clinical overview," Semin. Oncology, 14:1 (1987).

O. Martinez–Maza, "HIV–Induced Immune Dysfunction and AIDS–Associated Neoplasms," in Biological Approaches to Cancer Treatment: Biomodulation, M. Mitchell Editor, McGraw–Hill, Inc., Chapter 9, pp. 181–204 (1993).

Engel et al., "Mitogen–induced hyperproliferation response of peripheral blood mononuclear cells from patients with severe generalized perdiodontitis: Lack of correlation with proportions of T cells and T cell subsets," Clinical Immunol. Immunopathol., 30:374 (1984).

Miller, "Age–associated decline in precursor frequency for different cell–mediated reactions with preservation of helper and cytotoxic effect per precursor cell," J. Immunology, 132:63 (1984).

Saltzman and Peterson, "Immunodeficiency of the elderly," Review Infectious Disease, 9:127 (1987) was cited on p. 5 of the specification.

Biological Approaches to Cancer Treatment: Biomodulation, M. Mitchell Editor, McGraw–Hill, Inc. (1993) J. Rubin and M. Lotze, "Adoptive Cellular Immunotherapy of Cancer," Chapter 16, pp. 379–409, supra.

O'Flynn et al., Eur. J. Immunol., 1985, 15:7–11.

EX VIVO ACTIVATION OF IMMUNE CELLS

CROSS REFERENCE TO RELATED APPLICATIONS

This application is a continuation-in-part of U.S. patent application Ser. No. 08/214,400, filed Mar. 16, 1994, now U.S. Pat. No. 5,569,585 which is a continuation-in-part of U.S. patent application Ser. No. 08/030,607, filed Mar. 12, 1993, now abandoned, which is a continuation-in-part of U.S. patent application Ser. No. 07/963,486, filed Oct. 21, 1992, now abandoned.

This application is also a continuation-in-part of U.S. patent application Ser. No. 08/188,262, filed on Jan. 27, 1994, which is a continuation-in-part of U.S. patent application Ser. No. 07/936,730, filed on Aug. 31, 1992, now abandoned, which is a continuation of U.S. patent application Ser. No. 07/518,322, filed on May 7, 1990, now abandoned, which is a continuation of U.S. patent application Ser. No. 07/068,413, filed on Jul. 1, 1987, now abandoned, which is a continuation-in-part of U.S. patent application Ser. No. 06/696,546, filed on Jan. 30, 1985, now U.S. Pat. No. 4,716,111, which is a continuation of U.S. patent application Ser. No. 06/407,236, filed on Aug. 11, 1982, now abandoned.

This application is also a continuation-in-part of U.S. patent application Ser. no. 08/300,982 filed on Sep. 6, 1994 which is a continuation of U.S. patent application Ser. No. 07/975,682, filed Nov. 13, 1992, now abandoned, which is a divisional of U.S. patent application Ser. No. 07/747,484, filed Aug. 19, 1991, now U.S. Pat. No. 5,192,537, which is a continuation of U.S. patent application Ser. No. 07/681,668, filed Apr. 8, 1991, now abandoned, which is a continuation of U.S. patent application Ser. No. 07/405,044, filed Sep. 11, 1989, now abandoned, which is a continuation of U.S. patent application Ser. No. 06/903,489, filed Sep. 4, 1986, now abandoned, which is a continuation-in-part of U.S. patent application Ser. no. 06/595,081, filed Mar. 30, 1984, now abandoned. The above-referenced applications are incorporated herein by reference.

BACKGROUND OF THE INVENTION

This invention relates to immunotherapy.

Adoptive immunotherapy as an approach to treating cancer has been evolving rapidly over the past two decades. Beginning in the 1980's, IL-2 and lymphokine-activated killer (LAK) cell-based immunotherapies were shown to induce tumor responses in patients with melanoma and renal cell carcinoma (Rosenberg et al., 1985, N. Eng. J. Med. 313:1485–1492; Rosenberg et al., 1986, Important Advances in Oncology, DeVita et al., eds, Philadelphia, Lipincott, p. 55; Schoof et al., 1988, Cancer Res. 48:5007–5010; West et al., 1987, N. Engl. J. Med. 316:898–905). However, these therapies require systemic administration of high dose IL-2 which usually is accompanied by severe toxicity (Siegel et al., 1991, J. Clin. Oncol. 9:694–704; Margolin et al., 1989, J. Clin. Oncol. 7:486–498). More recently, tumor infiltrating lymphocytes (TIL) isolated from surgically removed tumors were utilized for adoptive immunotherapy following ex vivo activation and expansion (Rosenberg et al., 1986, Science 223:1318–1321; Kradin et al., 1989, Lancet 1:577–580; Speiss et al., 1987, J. Natl. Cancer Instit. 79:1067–1075; Rosenberg et al., 1988, N. Engl. J. Med. 319:1676–1688). Although treatment of patients with TIL has been shown to achieve somewhat higher tumor response rates relative to LAK therapy for melanoma (Rosenberg et al., 1986, Science 223:1318–1321; Kradin et al., 1989, Lancet 1:577–580; Spiess et al., 1987, J. Natl. Cancer Instit. 79:1067–1075; Rosenberg et al., 1988, N. Engl. J. Med. 319:1676–1688), this type of therapy has not shown consistent outcomes in clinical trials of other tumors. Furthermore, the limited availability of sufficient numbers of lymphocytes from autologous tumor tissue and other problems associated with long term, high volume cell culture have also restricted the application of TIL therapy.

SUMMARY OF THE INVENTION

The invention provides a novel, safe, and cost-effective method of nonspecifically enhancing a cell-mediated immune response to specific antigens or foreign substances in the body, including cancer cells. The process involves removing a patient's mononuclear cells and exposing the cells in vitro to substances which enhance the immune function of the cells. The ex vivo activated (EVA) cells are then reinfused into the patient to enhance the patient's immune responses and to treat various forms of cancer, infectious diseases, autoimmune diseases, or immune deficiency diseases.

The invention features a process of producing a population of immunoreactive cells by (a) contacting a sample of mononuclear cells derived from a patient, e.g., peripheral blood mononuclear cells (PBMC), with OKT3 at or below 37° C. to produce an OKT3-derived culture supernatant (T3CS); (b) removing the T3CS from the sample of patient-derived mononuclear cells; (c) determining the concentration of OKT3 in the T3CS, and if required, supplementing the T3CS with additional OKT3 to achieve a concentration of at least 0.1 ng/ml; (d) providing a second sample of mononuclear cells derived from the patient; and, (e) contacting the second sample of cells with the previously-generated T3CS for a period of time sufficient to yield a population of immunoreactive cells.

A sample of patient-derived mononuclear cells may contain T cells, B cells, monocytes and macrophages as well as other immune cells such as polymorphonuclear leukocytes, neutrophils, eosinophils, natural killer cells, and stem cells. Mononuclear cells may be derived from the peripheral blood of the patient, or other sites, e.g., a tumor or tumor-draining lymph node.

T3CS is a conditioned medium containing a mixture of autologous cytokines together with OKT3. The autologous cytokines mixture preferably promotes the growth and differentiation of Th1-type T cells, rather than Th2-type T cells. The OKT3 which is preferably in solution phase catalyzes the polyclonal activation of T cells, while the cytokines act synergistically as co-stimulants to optimize the overall degree of activation. The presence of both OKT3 and cytokines prevents the generation of T cells that are anergic or apoptotic and overcomes signal transduction defects in mononuclear cells derived from patients with cancer or chronic infectious diseases.

By the term "immunoreactive cells" is meant polyclonal T cells that exist in a primed state of activation. Primed cells are multifunctional, i.e., they possess an enhanced capacity to proliferate and produce cytokines upon further stimulation. The primed state of activation of the immunoreactive cells induced by culture in the OKT3-autologous cytokine mixture can be identified by measuring the stable biochemical changes, e.g., expression of growth, differentiation, and activation markers, which occur both on the cell surface and intracellularly. Immunoreactive cells of the invention have enhanced immunologic effector function, e.g., helper activity (CD4+T cells) or cytotoxicity (CD8+T cells). compared to unprocessed patient-derived mononuclear cells.

Immunoreactive cells have a low spontaneous level of immune function following processing, but are highly sensitized to respond to low doses of second signals upon further culture, or in vivo. The immunoreactive cells of the invention therefore require further exposure to an immune stimulant, such as an antigen; target cell, e.g., a tumor cell or virus-infected cell; an inflammatory molecule; an adhesion molecule; an immune cell, e.g., an accessory cell; a cytokine; or any combination thereof, to achieve full immunologic effector function. The immunoreactive cells of the invention are multifunctional, polyclonally-activated T cells which have been generated independent of disease-specific antigens utilizing a mixture of nonspecific lymphocyte activators, i.e., autologous cytokines, and a mouse monoclonal antibody, i.e. OKT3, as synergistic stimulants.

Suppressor cells in a population of patient-derived mononuclear cells may be inactivated by contacting the second sample with a suppressor cell inhibitory compound, e.g., cimetidine, indomethacin, cyclophosphamide, ranitidine, pepsid, or any combination thereof. Other histamine type-2 receptor blockers may also be used alone or in combination with the compounds listed above. Cimetidine and indomethacin are preferably used together at concentrations of $5 \times 10^{-5}$M (±2-fold) and $0.8 \times 10^{-8}$M (±2-fold), respectively.

The concentration of OKT3 used in the process of the invention is an amount that promotes activation of the patient's cells, but leaves minimal surface-bound OKT3 on the activated cell product. Minimizing the amount of surface-bound OKT3 on the immunoreactive cells in turn minimizes human anti-mouse antigen (HAMA) immune responses and rapid clearance of the immunoreactive cells from the circulation of a patient undergoing therapy with the immunoreactive cells of the invention. The concentration of OKT3 is preferably greater than 0.1 ng/ml but less than 25 ng/ml, more preferably 1-25 ng/ml, and most preferably 10-15 ng/ml. In addition to OKT3, any compound that binds to the T cell receptor or the T cell receptor-associated CD3 molecule on the cell surface may be used to stimulate the first sample of patient-derived mononuclear cells to produce T3CS.

Culture of the first sample with OKT3 is carried out for a period of time sufficient to produce a mixture of nonspecific lymphocyte activators capable of promoting the OKT3-catalyzed activation and differentiation of the second sample of patient-derived mononuclear cells into a population of immunoreactive cells. The culture period may range from 1 to 7 days and is preferably 3 days. The length of culture of the first sample may be adjusted, e.g., prolonged, to achieve the desired concentration of a nonspecific lymphocyte activator, e.g., a cytokine, e.g., tumor necrosis factor-alpha (TNFA) or interleukin-2 (IL-2), in the T3CS.

Culture of the second sample of patient-derived cells with T3CS is carried out for a period of time sufficient to produce a population of immunoreactive cells. As discussed above, the immunoreactive cells are in a primed state of activation, i.e., the cells are no longer in a resting state but require an additional stimulus, e.g., exposure to an antigen or other immune stimuli, to achieve a fully activated state characterized by enhanced immune function compared to unprocessed cells. Full activation of immunoreactive cells may be measured by expression of new cell surface markers, e.g., CD25, secretion of lymphokines, e.g., IFNγ, GM-CSF, or TNFα, cellular proliferation, or cellular differentiation into effector cells, e.g., cytolytic T cells or helper T cells.

Culture of patient-derived mononuclear cells with T3CS may be carried out for a period of 1 to 30 days, preferably 5 days. In the absence of antigen, the length of the culture period may be as short as 1-3 days; in the presence of antigen, the cells may be co-cultured for a period of 1 to 30 days. The length of culture may be adjusted, e.g., prolonged, to achieve the desired level of activation of the immunoreactive cells.

The invention also features a process of producing a population of immunoreactive cells by (a) providing a first sample of mononuclear cells derived from a patient; (b) determining the concentration of Fc-receptor positive accessory cells in the first sample, and if required, supplementing the first sample with a second sample of mononuclear cells derived from the same patient to achieve a concentration of 0.1–50% Fc-receptor positive accessory cells in the first sample; (c) contacting the first sample with OKT3 at or below 37° C. to produce a T3cs; (d) removing the T3CS from the first sample; (e) determining the concentration of OKT3 in the T3CS, and if required, supplementing the T3CS with OKT3 to achieve a concentration of at least 0.1 ng/ml; (f) providing a third sample of mononuclear cells derived from the same patient; (g) contacting the third sample with T3CS for a period of time sufficient to activate the third sample in vitro to yield a population of immunoreactive cells. The Fc-receptor positive cells are preferably monocytes, but may be granulocytes or dendritic cells. The concentration of patient-derived monocytes is preferably 0.1–50%, more preferably 1–30%, more preferably 5–15%, and most preferably 10% of the cells in the sample. The second sample of patient-derived mononuclear cells may be enriched for monocytes using cell fractionation techniques known in the art, e.g. panning or FACS, prior to augmenting the concentration of monocytes in the first sample.

In another aspect, the process is carried out by: (a) contacting a first sample of mononuclear cells derived from a patient with OKT3 at or below 37° C. to produce a T3CS; (b) removing the T3CS from the first sample; (c) determining the concentration of tumor necrosis factor-alpha (TNFα) in the T3CS, and if required, supplementing the T3CS with TNFα to achieve a concentration of at least 5 pg/ml; (d) providing a second sample of mononuclear cells derived from the same patient; (e) inactivating suppressor cells in the second sample; and, (f) contacting the second sample with T3CS and for a period of time sufficient to activate the second sample in vitro to yield a population of immunoreactive cells. The concentration of TNFα is preferably in the range of 100 pg/ml to 100 ng/ml, more preferably in the range of 100 pg/ml to 3000 pg/ml, and most preferably in the range of 500 pg/ml to 1000 pg/ml. The concentration of a cytokine, e.g., TNFα, may be augmented by (1) altering the length of the T3CS-generation step, (2) supplementing T3CS with purified non-recombinant cytokine, (3) supplementing T3CS with a recombinant cytokine, or (4) increasing the concentration of a cytokine-producing patient-derived mononuclear cell. The T3CS generation step (step (a)) of the process may be carried out for 1-7 days and is preferably carried out for 3 days.

In yet another aspect, the process requires after step (b), determining the concentration of both TNFα and OKT3, and if required, supplementing the T3CS with TNFα to achieve a concentration of at least 5 pg/ml TNFα and with OKT3 to achieve a concentration of at least 0.1 ng/m OKT3.

The levels o

The levels of interferon-gamma (IFN-γ), interleukin-4 (IL-4), and interleukin-10 (IL-10) in T3CS may be adjusted to achieve optimal generation of a particular type of immunoreactive cell, e.g., a Thi-type T cell. Accordingly, the process may include the steps of: (a) contacting a first sample of mononuclear cells derived from a patient with OKT3 at or below 37° C. to produce a T3CS; (b) removing the T3CS from the first sample; (c) determining the concentration of IFN-γ, IL-4, and IL-10 in the T3CS, and if required, adjusting the concentration of IFN-γ to at least 500 pg/ml, the concentration of IL-4 to less than or equal to 20 pg/ml, and the concentration of IL-10 to less than or equal to 20 pg/ml; (d) providing a second sample of mononuclear cells derived from the same patient; (e) inactivating suppressor cells in the second sample; and, (f) contacting the second sample with T3CS and for a period of time sufficient to activate the second sample in vitro to yield a population of immunoreactive cells.

The process of the invention may also include a step in which the state of activation of the immunoreactive cells is evaluated prior to administration of the cells to the patient. The cells may be evaluated phenotypically or functionally, i.e., by measuring the expression of a cell surface marker indicative of cell activation and/or differentiation or by measuring cell proliferation in response to an additional immune stimulus, e.g. antigen or phorbol myristate acetate (PMA). For example, following cell processing according to the invention, the number of CD25-positive cells in the population of immunoreactive T cells may be measured and the cells discarded if the number is less than 10% of the total number of T cells in the population. Preferably the number of CD25+ cells is at least 20% of the total number of T cells in the population.

The level of activation of the immunoreactive cells may also be evaluated by measuring proliferation in response to further stimulation by immune stimulants. The cells are discarded if the level of proliferation, e.g., the amount of $^3$H-thymidine incorporated into cellular DNA, is less than twice the level of proliferation of a sample of unprocessed mononuclear cells. The level of proliferation of the immunoreactive cells is at least twice that of unprocessed cells and preferably is 5-fold greater than that of unprocessed patient-derived cells. If necessary, the level of activation of the immunoreactive cells may be adjusted, e.g., to a higher level of activation, by altering the length of the patient-derive mononuclear cell-T3CS co-culture period to generate the immunoreactive cells, or alternatively, by adding fresh T3CS.

The mixture of nonspecific autologous lymphocyte activators and OKT3, i.e., T3CS, preferably contains: interleukin-1-alpha (IL-1α), interleukin-1-beta (IL-1β), interleukin-6 (IL-6), interleukin-8 (IL-8), TNFα, tumor necrosis factor-beta (TNFβ), interferon-gamma (IFNγ), granulocyte macrophage-colony stimulating factor (GM-CSF), monocyte/macrophage colony stimulating factor (M-CSF) and OKT3. In preferred embodiments, T3CS contains 12.7 ng/ml (±10–40%) OKT3 in addition to autologous cytokines in the following amounts (±10%–40%): IL-1α (105 pg/ml), IL-162 (1433 pg/ml), IL-6 (808 pg/ml), IL-8 (213 ng/ml), TNFα (570 pg/ml), TNFβ (171 pg/ml), IFNγ (14350 pg/ml), M-CSF (1193 pg/ml), and GM-CSF (840 pg/ml). IL-2, interleukin-3, IL-4, interleukin-7, IL-10, IL-12, T cell growth factor-beta (TGFβ), and granulocyte-colony stimulating factor may each be present in T3CS at a concentration of less than 20 pg/ml. Preferably, these cytokines are present at a concentration of less than 5 pg/ml. At least a 20% increase in the number of CD25+T cells in the first sample of patient-derived mononuclear cells following a T3CS-generation culture compared to a sample of uncultured mononuclear cells is predictive of sufficient production of autologous cytokines.

To avoid differentiation of the patient-derived mononuclear cells into lymphokine-activated killer (LAK) cells, the concentration of IL-2 must be less than 100 units/ml. The concentration of IL-2 in T3CS is preferably less than 50 units/ml, and more preferably in the range of 10-20 units/ml, and most preferably in the range of 1–5 ng/ml (1 unit of IL-2 is approximately equal to 250 pg/ml).

To generate optimal levels of antigen-independent non-specific lymphocyte activators, production of T3CS is preferably carried out at a temperature greater than 29° C. but less than 37° C., e.g., 35° C., for a period of 2 days. Co-culture of patient-derived mononuclear cells with T3CS to generate the immunoreactive cells may also be carried out at sub-physiologic temperature, e.g., a temperature greater than 29° C. but less than 37° C.

Following the incubation of cells with T3CS, the cells may be removed from the T3CS and contacted with IL-2, preferably in an amount which is sufficient to bind to at least 25% of the IL-2 receptors on the surface of the immunoreactive cells; more preferably, the amount of IL-2 is sufficient to saturate the IL-2 receptors on the surface of the immunoreactive cells. Contacting the immunoreactive cells with IL-2 is preferably done at 4° C., e.g., during storage or delivery of the cells prior to administration to the patient.

The invention also features a process of producing a population of antigen-specific polyclonal T cells by (a) contacting a first sample of mononuclear cells derived from a patient with OKT3 at or below 37° C. to produce a T3CS; (b) removing the T3CS from the first sample; (c) determining the concentration of OKT3 in the T3CS, and if required, supplementing the T3CS with additional OKT3 to achieve a concentration of at least 0.1 ng/ml; (d) providing a second sample of mononuclear cells derived from the same patient; (e) contacting the second sample with T3CS and an antigen for a period of time, e.g., 1–30 days, sufficient to activate the second sample in vitro to yield a population of antigen-specific polyclonal T cells. The concentration of OKT3 in the T3CS is preferably 0.1–1 ng/ml. To achieve the desired concentration, T3CS may be supplemented with OKT3, or OKT3 may be removed from T3CS using methods known in the art, such as chromatography, antibody-mediated depletion, or filtration. The antigen may be in the form of a natural or synthetic peptide, cell extract, a purified antigen, or a recombinantly expressed antigen and may be a tumor antigen, bacterial antigen, viral antigen, or autoantigen.

In another aspect, the invention provides an immunoreactive mononuclear cell produced by the inventive process. The cell is preferably a T cell, more preferably a Th1-type T cell. The T cell preferably expresses at least 10%, more preferably at least 75%, and most preferably at least 100% more cell-surface CD25 than an unprocessed mononuclear cell, e.g., a mononuclear cell in a resting state. The cell of the invention is preferably in a primed state, i.e., the cell proliferates at a rate that is at least twice that of an unprocessed T cell when contacted with an immune stimulant. The invention also includes a mixture of immunoreactive cells produced by the inventive process at least 75% of which are T lymphocytes, e.g., Th1-type T cells. The cells of the invention can be used to treat any condition characterized by sub-optimal immune responsiveness.

Another aspect of the invention features a process for producing a mixture of autologous nonspecific lymphocyte activators by collecting mononuclear cells from the blood of a patient afflicted with cancer or an infectious disease, inactivating suppressor T cells in the sample of mononuclear cells, and contacting the mononuclear cells with a compound that binds to the T cell receptor or the T cell receptor-associated CD3 molecule at or below 37° C., e.g., 29°–36° C., e.g., 35° C. for 2 days. The T cell receptor-binding compound may bind to the alpha chain or beta chain of a T cell receptor (or alternatively to the gamma or delta chain). The CD3-binding compound is preferably soluble OKT3, but may be any ligand that binds to the CD3 molecule on the surface of the cell. The cells may be contacted with the CD3-binding compound in the absence or in the presence of an antigen; the CD3-binding compound may be removed from the cell culture supernatant following the production of the mixture of autologous cytokines. In preferred embodiments, the mixture contains autologous cytokines in the following amounts (±10%–40%): IL-1α (105 pg/ml), IL-1β (1433 pg/ml), IL-6 (808 pg/ml), IL-8 (213 ng/ml), TNFα (570 pg/ml), TNFβ (171 pg/ml), IFNγ (14350 pg/ml), M-CSF (1193 pg/ml), and GM-CSF (840 pg/ml), either in the presence or absence of 12.7 ng/ml (±10–40%) OKT3.

The invention also includes the immunoreactive cells of the invention together with a pharmaceutically acceptable carrier or diluent for patient administration.

In yet another aspect, the invention features a method of treating a tumor or a viral pathogen in a patient by administering to the patient the immunoreactive cells of the invention. A suppressor cell inhibiting compound, e.g., cimetidine, indomethacin, or both, may be concurrently administered to the patient. The method may be used to treat any type of cancer including both solid tumors and hematologic tumors, e.g., renal cell carcinoma, breast carcinoma, prostate carcinoma, colo-rectal carcinoma, pancreatic carcinoma, ovarian carcinoma, melanoma and non-small cell carcinoma of the lung as well as leukemias and lymphomas. The methods and compositions of the invention represent a promising approach to tumors not treatable by conventional forms of therapy such as chemotherapy, radiation therapy, or surgery.

Mononuclear cells taken from a patient afflicted with a complex chronic viral disease may also be processed according to the invention to yield immunoreactive cells which can then be returned to the patient to augment the patient's immune response to the pathogen. Patients infected with pathogenic viruses, e.g., hepatitis B virus, hepatitis C virus, recurrent herpesvirus (herpes simplex virus, varicella zoster virus, cytomegalovirus), papilloma virus, Epstein Barr viurs and HIV (HIV-1 and HIV-2), may be treated in this manner.

Other features and advantages of the invention will be apparent from the following detailed description, and from the claims.

BRIEF DESCRIPTION

The figures will first be briefly described.

PROCESSING OF PERIPHERAL BLOOD MONONUCLEAR CELLS

Mononuclear cells to be processed according to the invention can be obtained from patients, e.g., those afflicted with a malignant tumor or an infectious disease such as hepatitis B. Peripheral blood or a mononuclear cell-enriched population of cells (obtained using known methods, e.g., apheresis) is taken from a patient, and a portion of the sample is mixed with an anticoagulant, e.g., heparin, sodium citrate, ethylenediaminetetraacetic acid, sodium oxalate. The blood-anticoagulant mixture then is diluted in a physiologically acceptable solution such as sodium chloride or phosphate buffered solution. Mononuclear cells are recovered by layering the blood-anticoagulant composition onto a centrifugation separation medium such as Ficoll-Hypaque (Pharmacia Corporation) or Lymphocyte Separation Medium (Litton Bionetics Corporation). The layered mixture then is centrifuged, and the interface containing the mononuclear cells is collected and washed.

The suppressor cells in the mononuclear cell population may be functionally inactivated by contacting the mononuclear cells with an agent that has a specific affinity for or effect upon suppressor cells. A particularly suitable composition for inactivating suppressor cells is an H2 receptor antagonist, such as cimetidine; a suitable composition for inactivating the suppressor activity of monocytes is indomethacin. Following suppressor cell inactivation, the mononuclear cells are suspended in a culture medium containing a mitogenic compound which binds to the T cell receptor or the T cell receptor-associated CD3 molecule, e.g., a CD3-binding compound, e.g., OKT3, to produce T3CS. Cimetidine may be used in the inventive process to inactivate suppressor cells. The addition of cimetidine to the medium when PBMC are cultured in the T3CS resulted in increased activation of T cells as measured by enhanced proliferative responses of immunoreactive cells upon further stimulation with PMA (data not shown).

In each sample, the concentration of mononuclear cells can be in the range of about $0.5$–$5.0 \times 10^6$ cells/ml, preferably $1$–$2 \times 10^6$ cells/ml. Although any standard tissue culture medium can be utilized in the process of this invention, the cells are preferably cultured under serum-free conditions at 37° C. using a standard tissue culture medium, e.g., AIM V medium available from Gibco-BRL, Grand Island, N.Y.

Mononuclear cells are generally cultured with OKT3 for a period of 3 days to generate T3CS. The T3CS may be used immediately or stored frozen and then thawed for use.

The concentration of cytokines, e.g., TNFα, or OKT3 concentration in the T3CS may be measured by any conventional means such as radioimmunoassay or enzyme-linked immunosorbent assay (ELISA) using antibodies specific for those components.

EXAMPLE 1
Characterization of T3CS
Generation of T3CS

Peripheral blood mononuclear cells (PBMC) were obtained from patients with mRCC by leukopheresis and fractionated using ficoll density separation. The cells from the mononuclear fraction were cultured at $1 \times 10^6$/ml in AIM V medium (Gibco-BRL, Grand Island, N.Y.) with 25 ng/ml OKT3 (Orthoclone OKT3; Ortho Pharmaceutical Corporation, Raritan, N.J.) for 3 days in Lifecell® bags. To inhibit suppressor cell activity, 50 μM cimetidine (Tagamet®; Smith Kline Beecham Pharmaceutical, Cidra, Pa.) and 10 nM indomethacin (Indocine; Merck Sharp & Dohme, West Point, Pa.) were also added to the culture medium. At the end of the culture, the culture bags were centrifuged at 1100×g for 20 min at room temperature, and the supernatants were collected, aliquoted, and stored at −70° C.

Composition of T3CS

The composition of the T3CS was determined by ELISA analysis using Quantikine kits from R&D Systems (Minneapolis, Minn.) for IL-αa, IL-2, 3, 4, 6, 7, 8, TNFα, TNFβ, GM-CSF, TGFβ and G-CSF, IFNγ kits from Endogen (Boston, Mass.) and Gibco (Grand Island, N.Y.), IL-10 kits from Biosource International (Camarillo, Calif.), and IL-1β kits from Cistron Biotechnology (Pine Brook, N.J.). IL-12 was determined by a bioassay (phytohemagglutinin (PHA) blast proliferation). The amount of OKT3 present in T3CS was determined by ELISA using the following reagents purchased from Vector Laboratories, Inc. (Burlingame, Calif.): Horse anti-mouse IgG to capture the OKT3 mouse mAb, biotinylated horse anti-mouse IgG to detect the captured mAb and ABC reagent consisting of avidin-conjugated horseradish peroxidase to amplify the signal. Ortho-phenylenediamine dihydrochloride (Sigma Chemical Co., St. Louis, Mo.) was used as a substrate.

Polyclonal Activation of PBMC

To evaluate EVA cells, cultures were carried out under the same conditions as used in processing patients-derived cells except on a smaller scale (5 ml). Excess PBMC obtained from mRCC patients were isolated by ficoll density gradient and were cultured at $2 \times 10^6$/ml for 5 days in complete AIM V medium (containing 50M cimetidine and 10 nM indomethacin) with either 25% (vol/vol) T3CS, or various concentrations of OKT3. Cells cultured with medium alone served as control. After incubation, the cells were washed and resuspended at a concentration of $10 \times 10^6$/ml in "infusion medium" (1% human serum albumin and 0.5% dextrose in Lactated Ringers solution). The cells were then stored overnight at 4° C. prior to analysis (to simulate overnight storage for final QA/QC and shipping to clinical sites).

Phenotypic Analysis of PBMC and EVA Cells

Cell phenotypes were determined by flow cytometry. Immunofluorescent staining was carried out using mAb specific for cell surface antigens, e.g., Coulterclones T3-RD1/CD3-RD1, T4-RD1, T8-RD1 and -FITC, IL-2R-FITC, I3-FITC and 2H4-RD1 (Coulter Corporation, Hialeah, FL), and Dako UCHL1-FITC (Dako corporation, Carpintera, Calif.). Appropriate isotype-matched labels were used as negative controls. Cells were resuspended at $2 \times 10^6$/ml in AIM V medium and aliquoted to 100 μl per tube. Two to four μls of labeled mabs were added to the cells according to the manufacturers' recommendation. The cells were then incubated with the Abs at 4° C. for 30 min, washed once with 500 μl of cold PBS, and resuspended at a concentration of $4 \times 10^5$ cells/ml in PBS for immediate analysis using a Coulter Epics Profile II flow cytometer.

PMA Assay

Proliferative responses to PMA were used to measure the degree of cell activation. The PBMC or EVA cells were resuspended to $1 \times 10^6$ cells/ml in AIM V medium with or without 1 ng/ml PMA, and cultured in triplicate in 96-well flat-bottom plates (Costar, Cambridge, Mass.) at 37° C. with 5% $CO_2$ for 48 hours. The cells were pulsed with $^3$H-thymidine (1 μCi /well) for the last 6 hours of culture, and harvested onto filtermats. The amount of radioactivity incorporated into the cells was determined by liquid scintillation counting.

Depletion of OKT3 or Cytokines From T3CS

T3CS was divided into 6 ml aliquots, and incubated with the appropriate neutralizing antibody (Goat anti-human, from R&D Systems) at 37° C. for one hour. The amount of antibody used for depletion was determined by the level of the particular cytokine known to be present and the antibody activity required for neutralization as specified by the manufacturer. Specifically, 125 μl of antibody was added for the depletion of IL-1β or TNFα, 20 μl for IL-6, 60 μl for IFN, 100 μl for GM-CSF, and 250 μl for IL-8. After incubation, 1 ml of pre-washed magnetic beads (Advanced Magnetics, Cambridge, Mass.) conjugated with either rabbit-anti-goat IgG (for cytokine depletion) or goat-anti-Mouse IgG (for OKT3 depletion) was added to the samples (2 ml of beads were used for multiple-cytokine depletion) and incubated with the cells at room temperature for 20 min. The cytokine-bound beads were then removed by placing the tube in a magnetic holder for 5 min. The cytokine-depleted T3CS was carefully transferred to a fresh labeled tube. The depletions were monitored by ELISA analysis.

Cytokine Composition of T3CS

As described above, T3CS was generated by culturing PBMC isolated from mRCC patients with 25 ng/ml OKT3 for 3 days. Aliquots of randomly selected mRCC patient T3CS (N=33–42) were analyzed for the presence of 17 different cytokines and OKT3 by ELISA. As shown in Table 1, T3CS contained a mixture of monokines and lymphokines including IL-1α, IL-1β, IL-6, IL-8, TNFα and β, IFNγ, M-CSF, and GM-CSF. Several other cytokines, including IL-2, 3, 4, 7, 10, 12, TGFβ, and G-CSF, were either undetectable or detected at very low levels in all samples tested. The cytokine profile indicated that the cells involved in the PBMC activation process were predominantly monocytes and Th1-type T cells (Seder et al., 1994, Ann. Rev. Immunol. 12:635–673) or T cells that had differentiated into Th1-type cytokine producers during the cultures. Although kinetic studies indicated that significant amounts of IL-2 (15–433 pg/ml) were present in all samples of T3CS analyzed during the first 24 hours of the culture, the level of IL-2 dropped sharply by day 2 (0–132 pg/ml). IL-2 levels became undetectable by day 3 when the culture supernatant was harvested. The drop in IL-2 is likely to be due to active consumption of the cytokine during cell culture. The mean OKT3 concentration in T3CS was 12.7 ng/ml. T3CS contains significantly lower levels of IL-2 than conventional conditioned media, e.g., PHA-generated cell supernatants, Concanavalin-A-generated cell supernatants, or mixed lymphocyte culture supernatants. Cytokine levels in T3CS from the majority patients fell into acceptable ranges, i.e., sufficient amounts of the key cytokines were present to produce immunoreactive cells in subsequent PBMC cultures. T3CS from a small number of patients contained low levels of certain cytokines. As discussed above, the concentration of cytokines may be augmented, if necessary, by carrying out the T3CS generating step for a longer period of time or alternatively, by adding recombinant or nonrecombinant cytokines.

TABLE 1

COMPOSITION OF CONDITIONED MEDIUM (T3CS)

| Cytokines: | | Mean | N |
|---|---|---|---|
| IL-1α | (pg/ml) | 105 | 33 |
| IL-1β | (pg/ml) | 1433 | 36 |
| IL-6 | (pg/ml) | 808 | 39 |
| IL-8 | (ng/ml) | 213 | 39 |
| TNFα | (pg/ml) | 570 | 39 |
| TNFβ | (pg/ml) | 171 | 39 |
| INFγ | (pg/ml) | 14350 | 40 |
| GM-CSF | (pg/ml) | 840 | 39 |
| M-CSF | (pg/ml) | 1193 | 39 |
| OKT3 | (ng/ml) | 12.7 | 42 |

IL-2, 3, 4, 7, 10, 12, TGFB and G-CSF are below detectable levels (<3–8 pg/ml) in >90% samples tested.

Accessory Cell Requirement for Production of Immunoreactive Cells

According to the invention, the concentration of patient-derived monocytes in a sample of patient-derived mononuclear cells, is preferably 0.1–50%, more preferably 1–30%, more preferably 5–15%, and most preferably 10%.

To evaluate the role of monocytes in cultures of patient-derived mononuclear cells, monocytes were depleted from patient-derived mononuclear cells using the well-known methods of adherence, e.g., to plastic plates, or incubation with L-leucine methyl ester. Incubation of a monocyte-depleted sample of patient-derived mononuclear cells with T3CS failed to yield the immunoreactive cells of the invention. In addition, blocking of the Fc receptor on the surface of Fc-receptor positive accessory cells, e.g., by adding an excess of soluble human polyclonal IgG to the patient-derived mononuclear cell-T3CS co-culture, inhibited the T3CS-catalyzed generation of immunoreactive cells by 93%. These data indicate that Fc-receptor positive accessory cells, i.e., monocytes, granulocytes or dendritic cells, are required to generate immunoreactive cells using the methods of the invention when OKT3 is used in solution phase.

If a sample of patient-derived mononuclear cells has a sub-optimal concentration of accessory cells, the sample of patient-derived mononuclear cells may be enriched for monocytes, granulocytes, or dendritic cells.

Role of Soluble OKT3

The OKT3 used in the process of the invention is preferably in solution phase rather than solid phase. One advantage of using soluble OKT3 in the inventive process is that soluble OKT3 mediates a more physiological interaction between Fc-receptor-bearing accessory cells, e.g., monocytes, and T cells. By forming a bridge between these cells, a full complement of costimulatory signals is initiated, thus minimizing the potential for the generation of incompletely (anergic) or aberrantly (apoptotic) activated T cells.
Enhancement of OKT3-Induced T Cell Activation by Autologous Cytokines The role of cytokines in the induction of T cell activation was compared to that of OKT3 alone. PBMC from seven mRCC patients were cultured for 5 days in AIM-V medium containing either 2.5 ng/ml OKT3 alone or 25% (vol/vol) T3CS that was first depleted of OKT3 and then reconstituted with 2.5 ng/ml of fresh antibody. This depletion/reconstitution approach was undertaken to assure that the amount of biologically active OKT3 in the T3CS would be identical to the OKT3 control. To avoid the bias from a single aliquot of T3CS, a pool made from three different mRCC patients was used to stimulate the PBMC from all seven patients.

The level of T cell activation was determined by the expression of cell surface IL-2 receptor (CD25) as measured by flow cytometry. FIGS. 1A-1E are representative immunofluorescence histograms that demonstrate that CD25 expression on T cells stimulated with the autologous cytokine-OKT3 mixture was significantly higher than that on T cells stimulated with OKT3 alone.
Primed Activation State of Immunoreactive Cells The degree of T cell activation was also assessed functionally by measurement of the proliferative response of EVA cells upon further stimulation by PMA, a protein kinase C activator.

Figure 4:
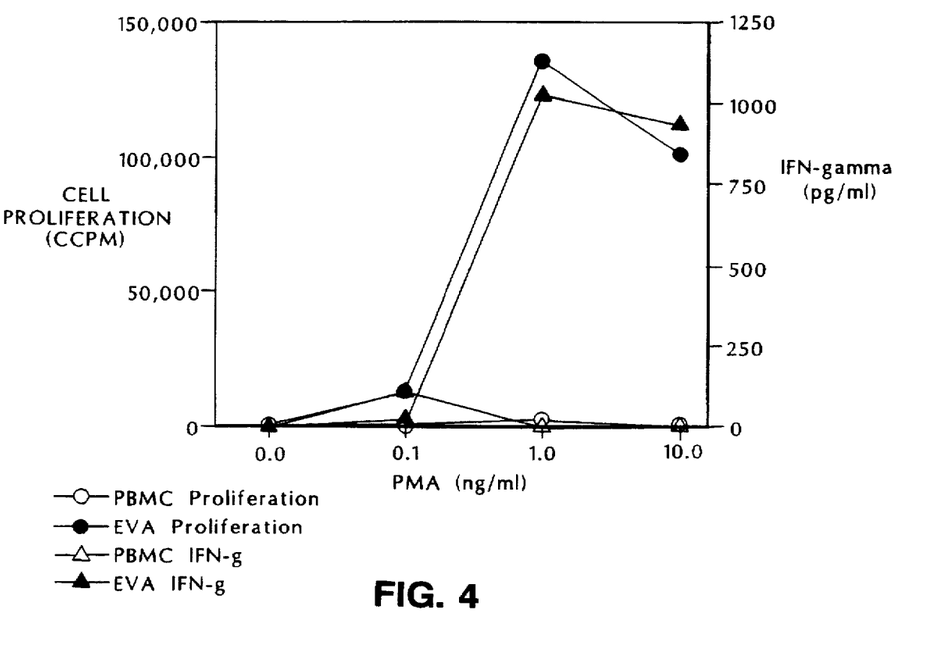
FIG. 4 is a line graph showing the enhanced capacity of EVA cells to proliferate and produce cytokines (IFNγ) upon stimulation with PMA compared to unprocessed mononuclear cells (PBMC).

FIG. 4 shows the results of an experiment in which immunoreactive cells were contacted with an immune stimulant, e.g., various concentrations of PMA. In the absence of further stimulation by PMA, immunoreactive cells displayed very little spontaneous proliferation or cytokine secretion when cultured at 37° C. in AIM V medium alone. However, when contacted with 1–10 ng/ml of PMA, immunoreactive cells (but not unprocessed PBMC) displayed an enhanced capacity to proliferate and produce IFNγ (as well as other Th1-type cytokines such as TNFα, TNFβ, and GM-CSF (data not shown)). These results are in contrast to those obtained with mononuclear cells activated by a conventional stimulant, such as PHA, which possess high levels of spontaneous proliferation and cytokine production following an initial 5-day activation culture (data not shown).

This enhanced proliferation and cytokine secretion upon contact with an immune stimulant and concomitant absence of or low levels of spontaneous proliferation and cytokine secretion indicates that the immunoreactive cells of the invention are in a primed state of activation.

Figure 5:
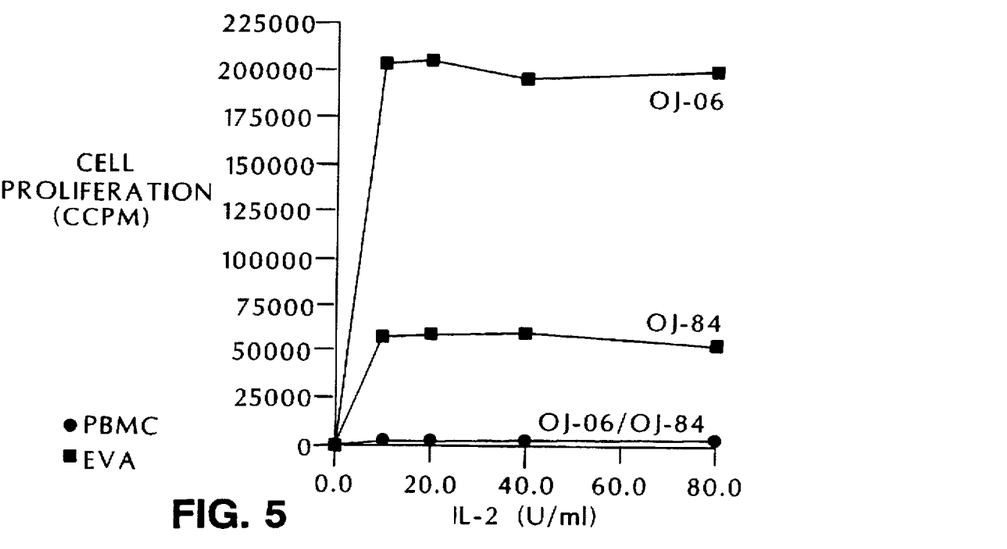
FIG. 5 is a line graph showing the enhanced capacity of EVA cells to proliferate upon stimulation with recombinant IL-2 compared to unprocessed mononuclear cells (PBMC).
Figure 7:
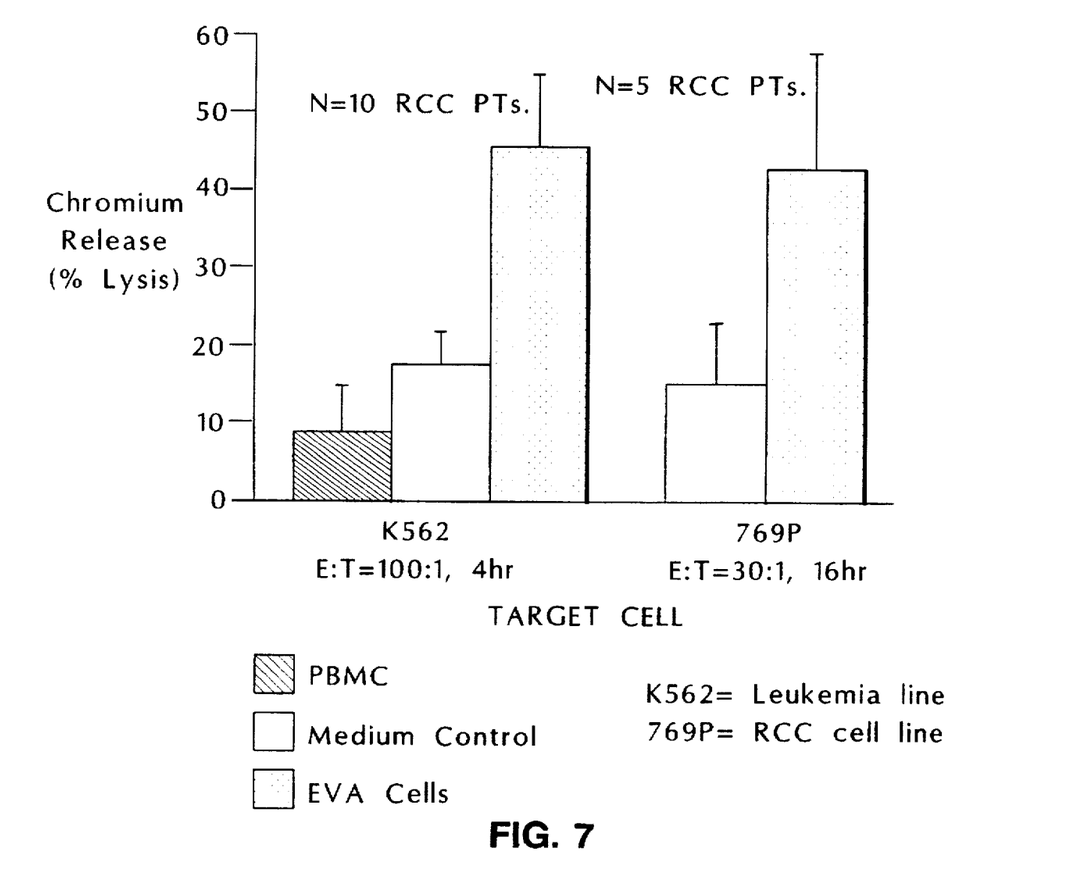
FIG. 7 is a bar graph showing the enhanced cytolytic function of EVA cells compared to unprocessed mononuclear cells (PBMC).

Similarly, an increase in proliferation was observed when EVA cells were contacted with another immune stimulant, i.e., IL-2 (FIG. 5). These data confirm the primed nature of the immunoreactive cells and suggest that the immunoreactive cells of the invention could be effectively co-administered with a low dose of IL-2.
Enhanced Effector Function of EVA Cells: Cytolytic T Cells The ability of the T3CS to support the generation of cytotoxic EVA cells was evaluated. As shown in FIG. 7, cytotoxicity was determined using a conventional chromium-51 release assay with the K562 leukemia cell line and allogeneic human renal carcinoma cell line 769P as targets. As shown in FIG. 7, EVA cells, i.e., T cells which have been polyclonally-activated independent of tumor-associated antigens according to the invention, possessed a greatly enhanced cytotoxicity toward both tumor lines compared to unprocessed PBMC. These in vitro results suggest that EVA cells are capable of directly killing tumor cells in vivo.

Enhanced Effector Function of EVA Cells: Helper T Cells

Figure 6:
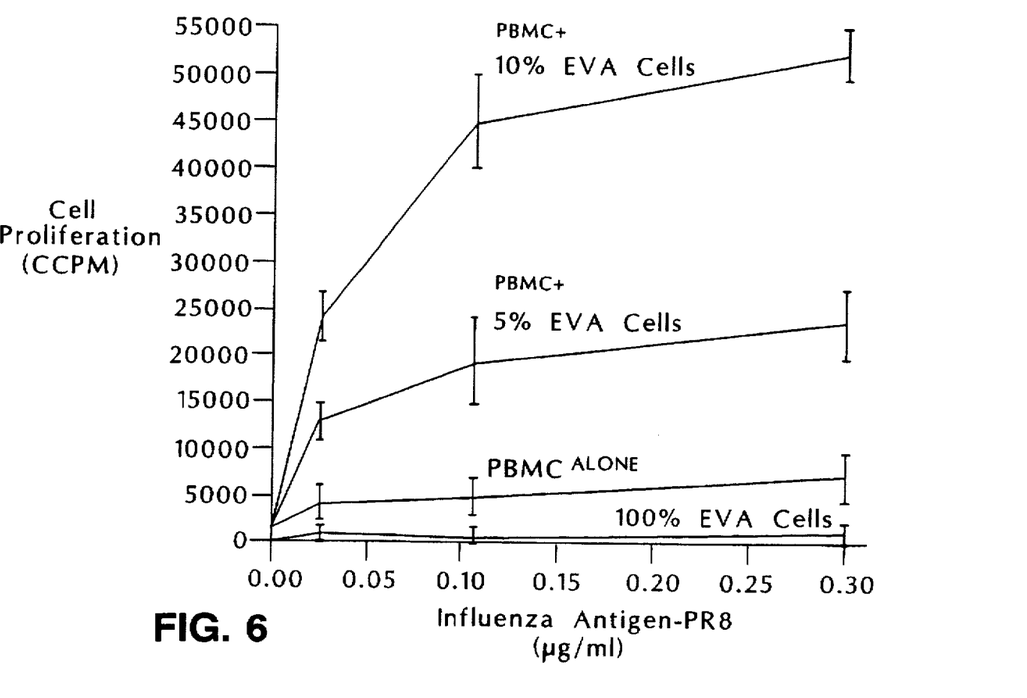
FIG. 6 is a line graph showing the enhancement of PBMC proliferation in response to a recall antigen (influenza) due to the addition of irradiated EVA cells as helper cells.

In addition to enhanced cytolytic function, the immunoreactive cells of the invention were found to have enhanced helper function. The ability of T3CS to support the generation of EVA cells with helper cell function was determined by measurement of the ability of irradiated EVA cells to enhance the proliferative response of unprocessed mononuclear cells upon stimulation by a recall antigen, e.g., an influenza antigen. As shown in FIG. 6, EVA cells added to cultures at low levels (5–10%) provided helper signals to unprocessed patient-derived mononuclear cells (presumably through the secretion of Th1-type cytokines) resulting in a significant increase in proliferation. These in vitro results suggest that EVA cells are capable of amplifying and broadening their effects in vivo through the production of cytokines.

The ability of EVA cells to proliferate and to produce a variety of cytokines (IL-2, GM-CSF, IFNγ, TNFα) in vitro in response to further stimulation by such agents as PMA and IL-2, as well as to lyse tumor cell targets, is greatly enhanced compared to the PBMC from which they were derived. The lowered activation threshold of the EVA cells exhibited in vitro suggests that once they are reinfused into patients, they are likely to demonstrate enhanced responsiveness to immunological signals, such as weakly immunogenic tumor antigens which normally are non-stimulatory to unprocessed cells.

Phenotypic Characterization of Immunoreactive Cells

Following short term (5-day) culture of patient-derived mononuclear cells in the autologous cytokine mixture/OKT3-containing conditioned medium, the resulting EVA cells were analyzed for the expression of cell surface antigens. EVA cells expressed enhanced levels of a variety of activation and/or differentiation markers on their cell surface including cytokine receptors, e.g., CD25, major histocompatibility complex (MHC) antigens, e.g., MHC class II, adhesion molecules/homing receptors, e.g., CD44/Leu8, costimulatory molecules, e.g., CD28, and markers of primed or memory T cells, e.g., CD45RO, as shown in Table 5.

Generation of Immunoreactive Cells: Synergistic Effects of Autoloa Cytokines Plus OKT3

Figure 1A:
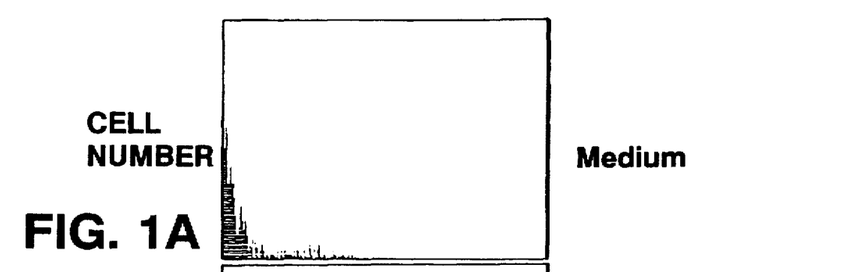
FIG. 1A is a flow cytometric histogram showing the level of cell surface CD25 on T lymphocytes cultured in culture media alone.
Figure 1B:
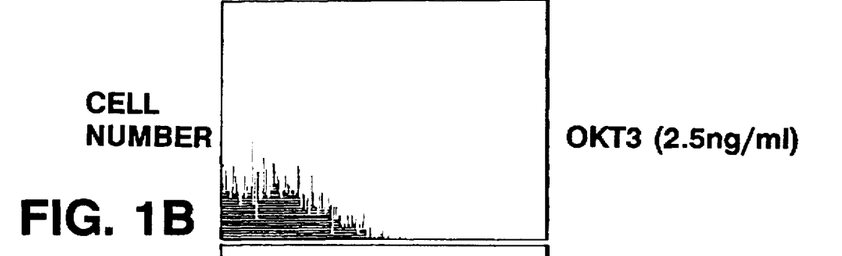
FIG. 1B is a flow cytometric histogram showing the level of cell surface CD25 on T lymphocytes activated by OKT3 alone.
Figure 1C:
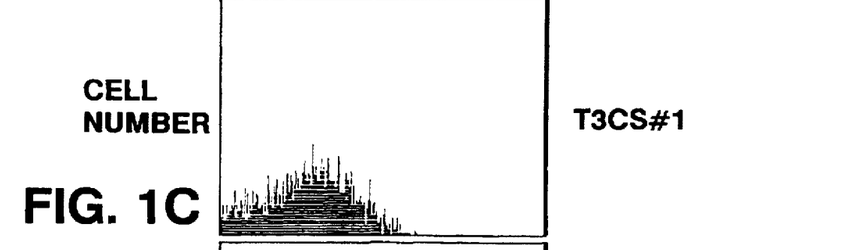
FIG. 1C is a flow cytometric histogram showing the level of cell surface CD25 on T lymphocytes activated with 25% (vol/vol) T3CS (patient #1).
Figure 1D:
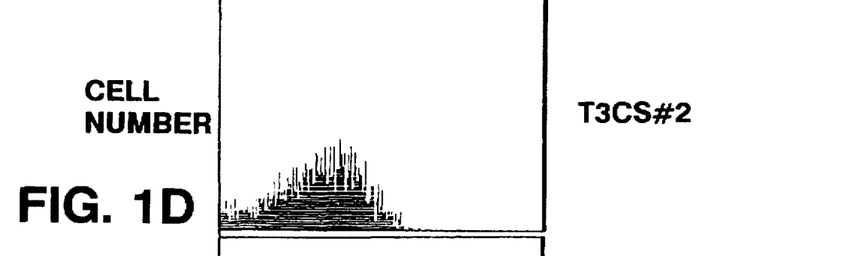
FIG. 1D is a flow cytometric histogram showing the level of cell surface CD25 on T lymphocytes activated with 25% (vol/vol) T3CS (patient #2).
Figure 1E:
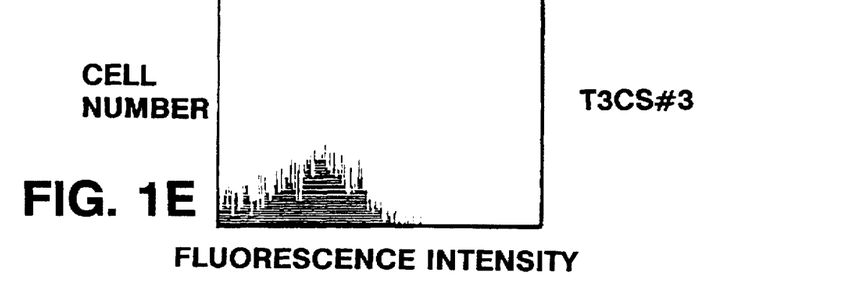
FIG. 1E is a flow cytometric histogram showing the level of cell surface CD25 on T lymphocytes activated with 25% T3CS (patient #3).
Figure 2A:
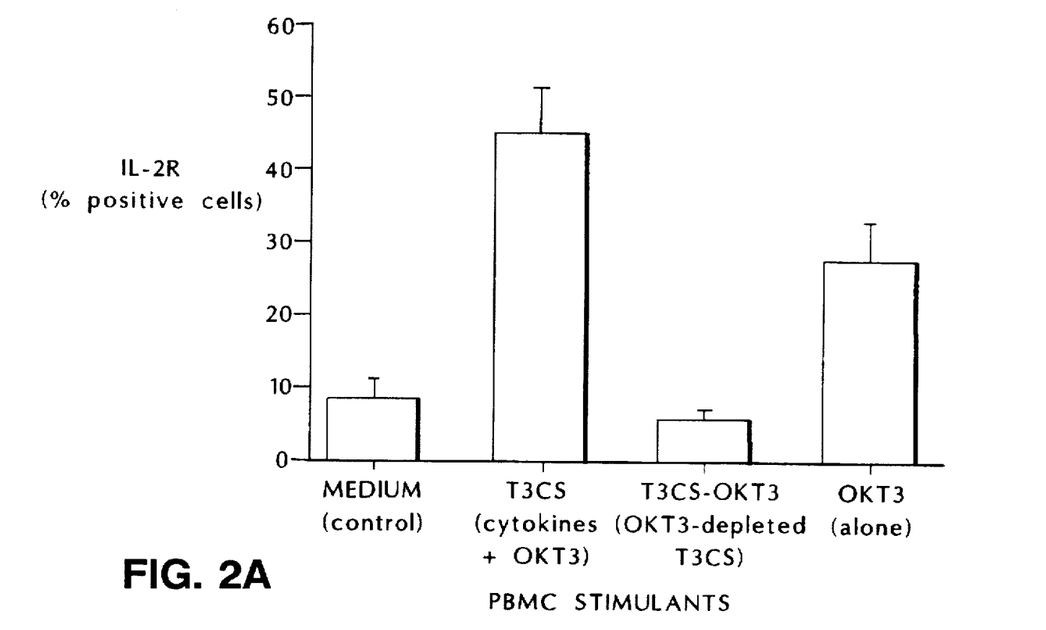
FIG. 2A is a bar graph showing cell surface CD25 (IL-2 receptor) expression of peripheral blood mononuclear cells (PBMC) obtained from 7 metastatic renal cell carcinoma (mRCC) patients following a 5-day culture with either 25% T3CS, OKT3-depleted T3CS, or OKT3 alone.
Figure 2B:
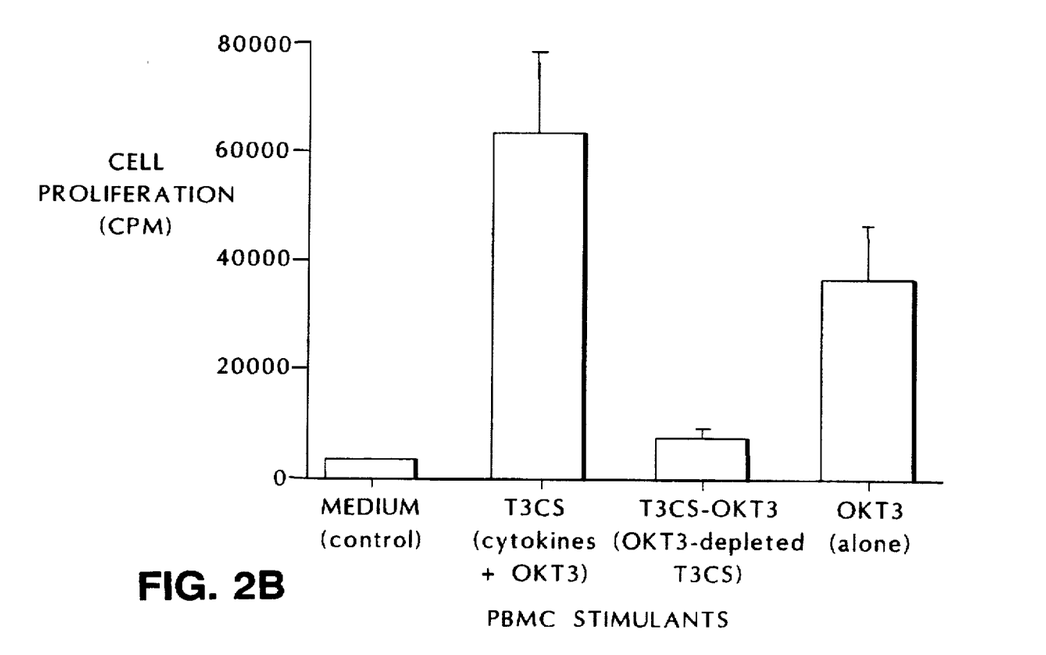
FIG. 2B is a bar graph showing PMA-induced proliferation of PBMC following a 5-day culture with 25% T3CS, OKT3-depleted T3CS, or OKT3 alone.

OKT3 was depleted from the T3CS in order to determine the relative effects of the anti-CD3 monoclonal antibody and the autologous cytokines on the induction of CD25 expression on the surface of T lymphocytes (FIG. 2A) and the proliferation of EVA cells upon further stimulation by PMA (FIG. 2B). Following depletion of OKT3 from the T3CS, there was little or no measurable activation of T cells, i.e., the autologous cytokines were not capable of stimulating resting PBMC in the absence of OKT3. However, when mRCC patient PBMC were cultured with complete T3CS, the cytokines functioned in synergy with OKT3 resulting in large increases in T cell activation relative to the levels achieved with OKT3 alone. Taken together, these results indicate that OKT3 catalyzes the generation of immunoreactive cells, while the autologous cytokines function as costimulants to optimize the overall T cell activation process.

TABLE 5

EVA CELL PRODUCT IDENTITY

| | % (+) LYMPHOCYTES | |
|---|---|---|
| | PBMC | EVA CELLS |
| CD3(+) – T CELLS | 75% | 84% |
| CD4(+) – HELPER T CELLS | 48% | 60% |
| CD8(+) – CYTOTOXIC T CELLS | 20% | 25% |
| CD3(+)/CD25$^{(+)}$ – ACTIVATED T CELLS (IL2 RECEPTOR – EARLY STAGE MARKER) | 3% | 44% |
| CD3(+)/CLASS II(+) – ACTIVATED T CELLS (MHC-LATE STAGE MARKER) | 13% | 42% |
| CD3(+)/CD45RO(+) – T CELLS (PRIMED "MEMORY" CELLS) | 49% | 69% |
| CD45RO(+)/CD25$^{(+)}$ – LYMPHOCYTES | 3% | 36% |
| CD3(+)/LEU 8(+) – T CELLS (LYMPH NODE HOMING RECEPTOR) | 31% | 59% |
| CD3(+)/CD28(+) – T CELLS (B7/BB1 RECEPTOR – COSTIMULATORY SIGNAL TRANSDUCTION) | 0.9* | 2.3* |
| CD3(+)/CD44(+) – T CELLS (EARLY ACTIVATION MARKER – CELL ADHESION MOLECULE) | 6.0* | 8.3* |

*Mean Channel Fluorescence Intensity
N = 19 mRCC Patient PBMC & EVA Cell Products Immunoreactive Cell Generation Utilizing Various Recombinant Cytokine-OKT3 Mixtures Reconstitution experiments were carried out to identify the cytokines in the T3CS that have the greatest effects on T cell activation. The roles of 5 major cytokines (IL-1β, IL-6, TNFα, IFN-γ, GM-CSF) were analyzed utilizing various combinations of recombinant cytokines together with OKT3. Table 2 shows the results of a series of experiments in which PBMC from 7 mRCC cancer patients were cultured in an allogeneic T3CS, OKT3 alone, or various OKT3-multiple recombinant cytokine mixtures. Five out of the six cytokines analyzed were found to enhance the level of stimulation of T cells compared to the level of stimulation seen with OKT3 alone, as measured by cell surface expression of CD25 on T cells. This result is consistent with the observation that the cytokines in T3CS act synergistically with the OKT3 catalyst in the activation process. Upon analyzing the data from individual mRCC patients, however, no single cytokine could be identified as the dominant costimulant across all cultures. In addition, for the majority of patient PBMC cultures, optimal T cell activation was achieved only with complete conditioned medium (T3CS). Taken together, these results indicate that a single recombinant cytokine, or even a mixture of several recombinant cytokines, is not able to provide the full complement of costimulatory signals required for optimal polyclonal activation of T cells. In contrast, use of a multiple autologous cytokine-enriched conditioned medium, i.e., T3CS, consistently resulted in the generation of optimally immunoreactive cells.

TABLE 2

Comparison of Conditioned Medium with OKT3 Plus Recombinant Cytokines on T Cell Activation in mRCC patients

| | | % CD25 Positive Cells | | | | | | | |
| | | | | | mRCC Patient | | | | |
| Stimulant | Average | #1 | #2 | #3 | #4 | #5 | #6 | #7 |
|---|---|---|---|---|---|---|---|---|
| Medium alone | 7 | 6.4 | 5.4 | 5.3 | 5.4 | 4.9 | 5.5 | 14.0 |
| OKT3 2.4 ng/ml | 38 | 18.8 | 24.7 | 54.7 | 28.6 | 31.7 | 64.1 | 46.3 |
| OKT3 + IL1* + TNFa* | 41 | 40.4 | 37.3 | 58.1 | 31.3 | 36.3 | 71.8 | 48.2 |
| OKT3 + IL1 + IFNg* | 44 | 32.3 | 37.1 | 59.7 | 16.4 | 39.1 | 71.9 | 51.9 |
| OKT3 + IL1 + GM-CSF* | 42 | 26.9 | 38.0 | 55.9 | 22.8 | 38.1 | 69.9 | 43.2 |
| OKT3 + IL1 + IL6* | 48 | 43.5 | 43.2 | 55.3 | 26.5 | 37.5 | 70.8 | 54.9 |
| OKT3 + IL1 + IFNg + GM-CSF | 45 | 33.5 | 44.4 | 58.4 | 21.6 | 34.8 | 68.7 | 41.9 |
| OKT3 + IL1 + TNFa + IL6 | 43 | 20.4 | 35.0 | 69.3 | 24.1 | 33.7 | 70.1 | 44.2 |
| OKT3 + IL1 + TNFa + GM-CSF | 43 | 26.1 | 40.7 | 66.3 | 21.8 | 33.3 | 67.5 | 42.2 |
| OKT3 + IL1 + IFNg + IL6 | 43 | 26.5 | 38.1 | 65.0 | 21.8 | 38.2 | 68.5 | 47.3 |
| OKT3 + IL1 + TNFa + GM-CSF + IL-6 | 41 | 27.6 | 39.7 | 61.2 | 18.8 | 39.7 | 73.1 | 40.8 |
| OKT3 + IL1 + TNFa + IFNg + IL-6 | 41 | 40.1 | 34.6 | 55.8 | 16.3 | 37.5 | 69.8 | 42.1 |
| OKT3 + IL1 + TNFa + IFNg + IL-6 + GM-CSF | 39 | 26.1 | 35.2 | 39.6 | 16.0 | 37.4 | 72.8 | 43.9 |
| 25% Conditioned Medium** | 54 | 53.3 | 56.4 | 69.4 | 57.3 | 33.2 | 74.8 | 33.8 |

PBMC from seven individual mRCC patients were cultured for 5 days with OKT3 alone, or OKT3 plus various combinations of cytokines, or with 25% of an allogeneic conditioned medium. The cells were stored at 4° C. overnight and then analyzed for CD25 expression by flow cytometry.
*Concentration of recombinant cytokines: IL-1b = 250 pg/ml, IL-6 = 100 pg/ml, TNFa = 100 pg/ml, IFNg = 250 pg/ml, GM-CSF = 250 pg/ml.
**25% conditioned medium (WP35) contains: OKT3 2.4 ng/ml, IL1b 650 pg/ml, IL6 400 pg/ml, TNFa 131 pg/ml, IFNg 1341 pg/ml, GMCSF 57 pg/ml.

TNFα Is an Important Co-stimulant for T Cell Activation

Table 3 shows the results from a series of experiments in which the contributions of various cytokines present in the T3CS to the overall T cell activation process was analyzed. The level of induction of CD25 on PBMC cultured in T3CS was compared to that achieved when cytokines were selectively depleted from aliquots of the same T3CS preparation.

Despite quantitative differences between the various RCC patient PBMC tested, depletion of TNFα from the T3CS consistently resulted in a reduction of CD25 expression on the EVA cells generated from all seven cancer patients, indicating that TNFA serves a key costimulatory function in enhancing OKT3-catalyzed polyclonal T cell activation.

The effects of the depletion of other cytokines from the T3CS were highly variable suggesting that the requirement for other costimulatory signals for optimal T cell activation varies from patient to patient, and perhaps even from culture to culture dependent upon the quality of the PBMC isolated at various points in time from different patients at different times along their disease course and upon the expression of cytokine receptors on freshly isolated mononuclear cells.

These results confirm that a single recombinant cytokine, or even a mixture of several recombinant cytokines, is not able to provide the necessary costimulatory signals for optimal polyclonal activation of T cells, and the complete spectrum of autologous cytokines in T3CS is necessary to generate the immunoreactive cells of the invention.

TABLE 3

Effect of Depletion of Various Cytokines from Conditioned Medium on T Cell Activation

| | IL-2 Receptor Expression (% of Control) | | | | | | |
| | Complete | Cytokine Depleted | | | | | |
| Patient # | Conditioned Media | TNFα | IL-1 | IL-6 | IL-8 | GM-CSF | IFNγ |
|---|---|---|---|---|---|---|---|
| 1 | 100 | 84 | 88 | 110 | 78 | 96 | 99 |
| 2 | 100 | 88 | 76 | 115 | 77 | 63 | 98 |
| 3 | 100 | 79 | 91 | 86 | 89 | 87 | 103 |
| 4 | 100 | 85 | 95 | 109 | 85 | 122 | 88 |
| 5 | 100 | 71 | 92 | 86 | 99 | 93 | 185 |
| 6 | 100 | 65 | 105 | 92 | 80 | 85 | 140 |
| 7 | 100 | 68 | 83 | 85 | 117 | 117 | 115 |
| Average | 100 | 77 | 90 | 98 | 89 | 95 | 118 |

PBMC from seven different mRCC patients were stimulated with 25% allogeneic conditioned media either complete or depleted with one of the cytokines listed. The cells were harvested 5 days later and examined for surface IL-2 receptor (CD25) expression by flow cytometry the next day. The effect of cytokine depletion is expressed as % of control which is the total IL-2R expression (% CD25 positive cells x mean channel fluorescence intensity) on cells activated by the complete, undepleted conditioned media.

T3CS was utilized as a nonspecific stimulant in the ex vivo generation of polyclonally activated T cells for the treatment of metastatic renal cell carcinoma. T3CS produced according to the invention contains a wide variety of monokines and lymphokines together with low levels of OKT3. OKT3 functions synergistically with the cytokines in the T3CS. Removal of OKT3 from the T3CS resulted in a substantial decrease of T cell activation demonstrating the role of anti-CD3 monoclonal antibody as a catalyst while the cytokines provide the costimulatory T cell activation signals.

Conditions in which OKT3 and autologous cytokines function synergistically in T cell activation have been achieved in serum-free medium. Serum-free culture is particularly desirable for the generation of EVA cells used in adoptive immunotherapy.

The claimed process employs aliquots of the T3CS generated in advance to be used as a stimulant in the secondary cultures. This approach ensurcomphat a full complement of costimulatory signals are available at the initiation of each activation culture and therefore minimizes the probability of generating anergic or apoptotic T cells. Furthermore, use of the pre-manufactured and quality-assured autologous cytokine-OKT3 mixture as a stimulant decreases the dependence upon de novo synthesis of cytokines during the early stage of the subsequent T cell activation cultures. Such decreased dependency is especially important under the conditions such as off-site cell processing that require shipping and storage of the cells, and when dealing the with cells from patients of various clinical stages.

PBMC obtained from individual cancer patients, and even PBMC taken from the same patient at different times, respond differently to various cytokines. OKT3-induced T cell activation for one patient's cells may strongly be affected by a given cytokine while cells from another patient are not affected at all by the same cytokine. This variation is due both to the inherent diversity of human lymphocytes and accessory cells, and to the fluctuation caused by the process prior to the activation such as collection of the cells by apheresis. overnight storage and shipping may affect accessory cell activity which in turn affects the dependence of the T cells on exogenous cytokine present in the culture. Hence, the methods of the invention require evaluation of various key components of the T3CS, e.g., OKT3 and TNFα concentration, and the concentration of accessory cells, e.g., monocytes. The methods may also require the evaluation of the activation state, i.e., PMA responsiveness, of the processed cells to predict their clinical effectiveness.

IL-2-Independent Generation of Immunoreactive Cells

Utilizing T3CS as a stimulant for mononuclear cells, it is possible to generate T cells expressing high levels of CD25/IL-2 receptors, independent of the inclusion of high levels of exogenous IL-2 in the culture medium. Although low levels of IL-2 are present in both the T3CS and EVA cultures at early timepoints, there is no detectable (<6 pg/ml) autologous IL-2 present in the T3CS when the EVA culture is initiated. Consequently, in contrast to LAK and TIL cells which are both cultured in high levels of IL-2, the immunoreactive cells generated by the inventive process are presumably less dependent upon systemic administration of high dose IL-2 for therapeutic efficacy. In addition, the lack of IL-2 in the T3CS allows the production of immunoreactive cells, i.e., multifunctional, polyclonal T cells containing both CD8+/cytotoxic T cells and a high percentage of CD4+/helper cells, in contrast to PBMC grown in high dose IL-2 which are highly enriched in CD8+/cytotoxic T cells. Thus, the immunoreactive cells of the invention have broader functional capacities than PBMC cultured in IL-2.

If production of T3CS containing low levels, e.g., up to 10 units/ml, of autologous IL-2 is desired to further enhance the generation of immunoreactive cells, IL-2 production may be increased and IL-2 consumption simultaneously decreased by modification of the culture conditions, such as the kinetics and temperature of the T3CS generation process.

Following processing, the immunoreactive cells may be exposed to IL-2 at 4° C. such that IL-2 binds to at least 25% of the cell surface IL-2 receptors. Preferably, the cell surface IL-2 receptors are saturated, i.e., 100% of the IL-2 receptors on the surface of a cell are bound to IL-2, with IL-2 prior to infusion into a patient.

Immunoreactive cells with cell surface bound IL-2 are likely to have an enhanced ability to expand in vivo and a decreased dependence upon helper cell-mediated IL-2 production, an activity which may be lacking or depressed in immunosuppressed cancer patients. In addition, administration of IL-2 to a patient in a cell-bound form avoids the toxicity and other clinical complications often associated with intravenous or subcutaneous co-administration of high dose IL-2 to support cell therapy.

OKT3

Intravenous OKT3 administration, utilized for the suppression of transplant graft rejection in humans, induces rapid (within 24 hours) removal of a high percentage of $CD3^+$ T cells from the circulation due to the presence of the foreign antibody molecules on the lymphocyte cell surface (Vigeral et al., 1986, Transplantation 41:730; Chatenoud et al., 1986, J. Immunol. 137:830–838). Excessive amounts of OKT3 bound to an EVA cell surface may accelerate the clearance of the T cells, resulting in decreased therapeutic efficacy. The use of T3CS as a stimulant minimizes this clinical problem because T cell activation can be achieved with a minimal concentration of OKT3 in the presence of autologous cytokines compared to the concentration required in the absence of autologous cytokines.

The use of the T3CS to stimulate PBMC allows a high level of T cell activation to be catalyzed by a minimal amount of OKT3 (1–4 ng/ml). The inventive methods leave very little detectable surface-bound antibody on the activated T cell product, and therefore decrease the probability of the EVA cells being rapidly removed from the circulation. In addition, the low level of surface-bound OKT3 allows more CD3-TCR complexes on the surface of the activated T cells to remain unoccupied so that key molecules such as MHC Class I and II molecules, tumor antigens, and immunogenic peptides may bind to and stimulate the T-cell receptor following re-infusion of the cells into patients. Stimulation of PBMC with higher concentrations of OKT3 tends to drive the cell culture towards CD8 cell dominance, whereas culture in the autologous cytokine-OKT3 mixture maintains a relatively high CD4/CD8 ratio which is desirable for the therapeutic function of EVA cells. Finally, the low level of cell-bound OKT3 reduces the danger of a patient developing HAMA responses after multiple infusions of EVA cells.

EXAMPLE 2

Effect of Temperature on Cytokine Production

Conditions under which patient-derived mononuclear cells are cultured with OKT3 to generate T3CS were analyzed. For the generation of T3CS, cells were cultured for a period of 1 to 5 days. As shown in table 4, it is possible to manipulate the time course and/or temperature at which T3CS is generated in order to selectively increase or decrease the levels of certain autologous cytokines.

The effect of temperatures ranging from 29° C. to 39° C. on the production of cytokines was also tested. As shown in Table 4, higher levels of cytokines were detected in cultures grown at temperatures of 37° C. or below.

EXAMPLE 3
Production and therapeutic administration of EVA cells

Human peripheral blood cells are collected by apheresis, and the PBMC are isolated using a Ficoll gradient. The PBMC are incubated at 37° C. at a concentration of $10^6$ cells/ml in AIM V medium containing cimetidine ($5\times10^{-5}$ mol/l), indomethacin ($10^{-8}$ mol/l), and 25 ng/ml OKT3 (Ortho Biotech, Raritan, N.J.). The activity of suppressor T cells and of suppressor monocytes is inactivated by culturing the PBMC with cimetidine and indomethacin. After three days, the culture supernatant, i.e., T3CS, is harvested, divided into portions, and frozen at -80° C. until required for use in the cell cultures.

A second sample of PBMC is collected from a patient, and suspended at approximately $2\times10^6$ cells/ml in AIM V medium containing 25% v/v T3CS, cimetidine ($5\times10^{-5}$ mol/l) and indomethacin ($10^{-8}$ mol/l). The cells are harvested following a five day culture at 37° C. in a moist-air incubator containing 5% $CO_2$, then resuspended at $10^7$ cells/ml. Following overnight storage of the activated cells at 40° C., approximately $10^9$ cells are reinfused intravenously at room temperature to the patient over 30 min.

If the concentration of OKT3 or TNFα or other cytokines in the T3CS are below the preferable ranges, the levels of one or more of the cytokines may be increased as follows. One way to increase the amount of a cytokine, e.g., TNFα, is to adjust, e.g., increase, the time of culture before harvesting the T3CS. Alternatively, the concentration of monocytes (which produce TNFα) may be increased in the T3CS-generating culture, or the temperature at which the T3CS-generating step is carried out may be adjusted to optimize TNFα production. Another way to increase the amount of a cytokine is to increase the percentage of T3CS added to the second sample of patient-derived mononuclear cells, i.e., by adding greater than 25% T3CS.

The therapeutic methods of the invention which utilize EVA cells may be used to treat mRCC and other types of metastatic cancers, as well as infectious diseases, autoimmune diseases, and immunodeficiency diseases. Clinical outcome may be assessed by such measures as length of patient survival, quality of life measurements, changes in any indicators of medical function such as clinical chemistries, size of tumors, changes in load of virus, bacteria, fungus, or parasite, toxicity of the therapy, or delay in time of recurrence of the disease, or other assessments. Clinical outcome may also be evaluated by monitoring changes in immune status or time to recurrence of a tumor in a cancer patient.

TABLE 4

Temperature/Timecourse Study

| Cytokine | Days | EC46 | | | | | | AVERAGE OF ALL FIVE PATIENTS | | | | | |
|---|---|---|---|---|---|---|---|---|---|---|---|---|---|
| | | 39° C. | 37° C. | 34° C. | 33° C. | 32° C. | 29° C. | Days | 39° C. | 37° C. | 34° C. | 33° C. | 32° C. | 29° C. |
| IL-2 | 1 | 521.4 | 557.8 | ND | 946.3 | ND | 831.6 | 1 | 183.9 | 304.7 | 406.1 | 758.8 | 363.1 | 434.9 |
| | 2 | 68.9 | 18.6 | ND | 441.2 | ND | 689.3 | 2 | 17.4 | 31.7 | 257.1 | 403.8 | 218.1 | 381.1 |
| | 3 | 6.0 | 1.3 | ND | 44.7 | ND | 228.0 | 3 | 3.5 | 2.5 | 78.9 | 53.8 | 43.4 | 204.3 |
| | 5 | 0.8 | 3.2 | ND | 1.8 | ND | 17.6 | 5 | 2.6 | 2.7 | 2.8 | 0.9 | 2.6 | 74.8 |
| TNFa | 1 | 1427.1 | 1819.5 | ND | 702.9 | ND | 592.2 | 1 | 569.9 | 993.1 | 568.3 | 593.6 | 525.5 | 319.5 |
| | 2 | 1237.2 | 1774.2 | ND | 1735.2 | ND | 668.1 | 2 | 469.6 | 1036.1 | 813.1 | 1634.6 | 1006.9 | 707.9 |
| | 3 | 1064.4 | 1318.2 | ND | 2134.8 | ND | 1861.5 | 3 | 276.9 | 478.3 | 672.5 | 2460.3 | 633.7 | 1170.8 |
| | 5 | 629.4 | 830.4 | ND | 2031.9 | ND | 2706.6 | 5 | 149.7 | 205.1 | 231.5 | 1612.8 | 188.1 | 1258.6 |
| IL-6 | 1 | 1031.2 | 740.0 | ND | 341.6 | ND | 198.4 | 1 | 422.8 | 420.7 | 432.4 | 311.2 | 270.8 | 122.2 |
| | 2 | 1657.6 | 1486.4 | ND | 1100.0 | ND | 597.6 | 2 | 653.9 | 804.5 | 751.3 | 1146.4 | 690.0 | 421.5 |
| | 3 | 1740.8 | 1537.6 | ND | 1581.6 | ND | 1076.0 | 3 | 626.2 | 741.4 | 822.8 | 1579.6 | 946.1 | 621.4 |
| | 5 | 1879.2 | 1438.4 | ND | 1738.4 | ND | 1448.0 | 5 | 542.8 | 522.2 | 533.5 | 1378.8 | 466.7 | 709.1 |
| GM-CSF | 1 | 292.8 | 306.4 | ND | 237.8 | ND | 233.6 | 1 | 416.6 | 455.1 | ND | 289.5 | ND | 270.5 |
| | 2 | 416.8 | 497.6 | ND | 351.0 | ND | 258.5 | 2 | 481.9 | 715.8 | ND | 530.0 | ND | 365.1 |
| | 3 | 549.3 | 590.6 | ND | 506.5 | ND | 487.4 | 3 | 345.6 | 397.1 | ND | 975.6 | ND | 601.7 |
| | 5 | 667.2 | 635.7 | ND | 685.5 | ND | 741.4 | 5 | 348.2 | 322.2 | ND | 669.1 | ND | 871.8 |
| gIFN | 1 | ND | ND | ND | ND | ND | ND | 1 | 370.3 | 899.9 | 497.2 | ND | 511.7 | 166.3 |
| | 2 | ND | ND | ND | ND | ND | ND | 2 | 1812.0 | 3839.3 | 1463.9 | ND | 1578.1 | 272.6 |
| | 3 | ND | ND | ND | ND | ND | ND | 3 | 1880.3 | 5232.8 | 3101.5 | ND | 3843.8 | 350.2 |
| | 5 | ND | ND | ND | ND | ND | ND | 5 | 931.5 | 4009.2 | 3086.2 | ND | 3192.4 | 830.7 |
| IL-1β | 1 | 925 | 782 | ND | 413 | ND | 297 | 1 | 462.8 | 795.8 | 633.3 | 409.5 | 563.0 | 304.2 |
| | 2 | 1,916 | 1,862 | ND | 1,532 | ND | 839 | 2 | 949.2 | 1658.0 | 1435.3 | 1179.5 | 1165.3 | 711.2 |
| | 3 | 1,675 | 1,747 | ND | 994 | ND | 453 | 3 | 683.6 | 1498.6 | 1540.3 | 944.0 | 1393.7 | 542.2 |
| | 5 | 1,780 | 1,653 | ND | 1,527 | ND | 1,169 | 5 | 535.2 | 1195.2 | 1430.0 | 1371.5 | 944.0 | 802.2 |
| OKT3 | 1 | 11.9 | 13.0 | ND | 13.9 | ND | 10.0 | 1 | 13.6 | 19.2 | 21.3 | 17.0 | 20.4 | 17.5 |
| | 2 | 9.4 | 8.7 | ND | 11.8 | ND | 10.7 | 2 | 19.5 | 15.9 | 20.9 | 15.9 | 19.7 | 17.2 |
| | 3 | 8.7 | 6.3 | ND | 8.8 | ND | 13.5 | 3 | 14.2 | 11.9 | 17.4 | 12.8 | 17.9 | 16.2 |
| | 5 | 6.0 | 4.8 | ND | 6.8 | ND | 10.9 | 5 | 11.7 | 7.6 | 12.1 | 10.0 | 11.6 | 15.5 |

EXAMPLE 4
Treatment of Hepatitis B Infection
Polyclonal Activation of PBMC from Chimpanzees with Chronic Hepatitis B Infection Viral hepatitis refers to an infection of the liver caused by a small group of hepatotropic viruses that may be differentiated serologically. Of the three serotypes, A, B and C; B and C cause far more serious infections than hepatitis A.

The methods of the invention were used to produce immunoreactive cells from mononuclear cells derived from chimpanzees infected with hepatitis B, a primate model of chronic viral infection. The chimpanzee model was chosen over the woodchuck or mouse model as the most relevant model of the human disease because chimpanzees can be experimentally infected with the human hepatitis B virus.

Figures 3A, 3B:
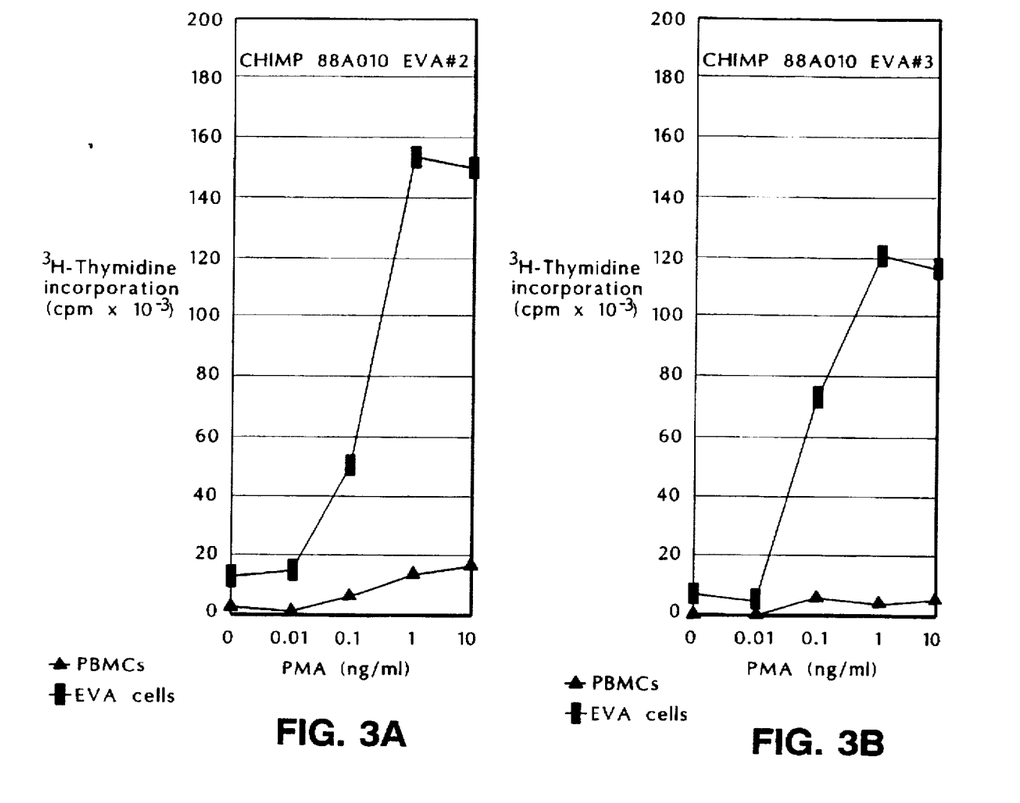
FIG. 3A is a line graph showing the enhanced capacity of chimpanzee EVA cells (EVA #2) to proliferate upon stimulation with PMA compared to unprocessed chimpanzee-derived mononuclear cells (PBMCs).
FIG. 3B is a line graph showing the enhanced capacity of chimpanzee EVA cells (EVA #3) to proliferate upon stimulation with PMA compared to unprocessed chimpanzee-derived mononuclear cells (PBMCs).

Mononuclear cells from chimpanzees with chronic hepatitis B were polyclonally activated with OKT3 to produce a T3CS. A second sample of mononuclear cells was cultured with T3CS to obtain EVA cells. Chimpanzee-derived mononuclear cells processed according to the invention yielded immunoreactive cells. As shown in FIGS. 3A and 3B, the immunoreactive cells were in a primed state of activation, i.e., they proliferated upon stimulation with PMA whereas unprocessed chimpanzee-derived mononuclear cells did not. In addition, the spectrum of phenotypic markers on the chimpanzee EVA cells was found to be similar to that on EVA cells produced from patient-derived mononuclear cells (data not shown). These data indicate that the methods of the invention can be used to generate immunoreactive cells from animals, e.g., patients, with chronic viral infections. These immunoreactive cells can then be re-infused into the patient to augment the patient's immune response to the pathogenic virus.

EXAMPLE 5
In vivo Use of T3CS

T3CS may also be used as a formulation for the in vivo delivery of cytokines. T3CS which has been depleted of OKT3 may be encapsulated in an appropriate slow release matrix, e.g., a liposome or biocompatible polymer, in order to maintain a critical level of cytokine over time and to minimize the toxicity associated with bolus-delivery of cytokines. In vivo delivery of T3CS may also be targeted to a particular site in the body for optimal effectiveness.

In vivo administration of T3CS offers several advantages over conventional cytokine therapy, i.e., administration of one cytokine. T3CS is a unique mixture of both monokines and lymphokines which initiate and promote activation and/or recruitment of several different immune cell types. Thus, T3CS can induce a full spectrum of immune responses in a patient.

Other embodiments are within the following claims.

What is claimed is:

1. A process of producing a population of immunoreactive cells comprising the steps of:
   (a) contacting a first sample of mononuclear cells derived from a patient with OKT3 at or below 37° C. to produce an OKT3-derived culture supernatant (T3CS);
   (b) removing said T3CS from said first sample;
   (c) determining the concentration of OKT3 in said T3CS, and if required, supplementing said T3CS with said OKT3 to achieve a concentration in the range of 1–25 ng/ml;
   (d) providing a second sample of mononuclear cells derived from said patient; and
   (e) contacting said second sample with said T3CS and said OKT3 for a period of time sufficient to activate said second sample in vitro to yield a population of immunoreactive cells.

2. The process of claim 1, wherein said OKT3 concentration is in the range of 10–15 ng/ml.

3. The process of claim 1, wherein step (a) is carried out for 6 hours-7 days.

4. The process of claim 3, wherein step (a) is carried out for 3 days.

5. The process of claim 1, wherein said period of time in step (e) is 1–30 days.

6. The process of claim 5, wherein said period of time in step (e) is 5 days.

7. The process of claim 1, further comprising after step (d), contacting said second sample with a suppressor cell inhibitory compound.

8. The process of claim 7, wherein said suppressor cell inhibitory compound is cimetidine, indomethacin, or both cimetidine and indomethacin.

9. A process of producing a population of antigen-specific polyclonal T cells comprising the steps of:
   (a) contacting a first sample of mononuclear cells derived from a patient with OKT3 at or below 37° C. to produce a T3CS;
   (b) removing said T3CS from said first sample;
   (c) determining the concentration of OKT3 in said T3CS, and if required, supplementing said T3CS with said OKT3 to achieve a concentration in the range of 0.1–25 ng/ml;
   (d) providing a second sample of mononuclear cells derived from said patient;
   (e) contacting said second sample with said T3CS and an antigen for a period of time sufficient to activate said second sample in vitro to yield a population of antigen-specific polyclonal T cells.

10. The process of claim 9, wherein said period of time is 1–30 days.

11. The process of claim 9, wherein said antigen is a tumor antigen.

12. The process of claim 9, wherein said antigen is a bacterial antigen, viral antigen, or autoantigen.

13. The process of claim 1, further comprising after step (e), contacting said second sample with IL-2.

14. The process of claim 13, wherein said second sample is contacted with said IL-2 at 4° C.

15. The process of claim 13, wherein said IL-2 is present in an amount sufficient to bind to at least 25% of the IL-2 receptors on the surface of said immunoreactive cells.

16. The process of claim 15, wherein said IL-2 is present in an amount sufficient to bind to 100% of the IL-2 receptors on the surface of said immunoreactive cells.

17. The process of claim 1, wherein step (e) is carried out below 37° C.

* * * * *